United States Patent
Kitami et al.

(10) Patent No.: US 8,725,432 B2
(45) Date of Patent: *May 13, 2014

(54) SIGNAL PROCESSING METHOD, SIGNAL PROCESSING APPARATUS, AND CORIOLIS FLOWMETER

(75) Inventors: Hirokazu Kitami, Tokyo (JP); Hideki Shimada, Tokyo (JP)

(73) Assignee: Oval Corporation, Tokyo (JP)

( * ) Notice: Subject to any disclaimer, the term of this patent is extended or adjusted under 35 U.S.C. 154(b) by 698 days.

This patent is subject to a terminal disclaimer.

(21) Appl. No.: 12/957,708

(22) Filed: Dec. 1, 2010

(65) Prior Publication Data

US 2011/0203388 A1    Aug. 25, 2011

(30) Foreign Application Priority Data

Feb. 19, 2010  (JP) ................................ 2010-034760

(51) Int. Cl.
    *G01F 1/00*  (2006.01)
(52) U.S. Cl.
    USPC .................................. 702/45; 702/50; 702/56
(58) Field of Classification Search
    USPC .................... 702/45, 50, 56; 324/600; 73/488
    See application file for complete search history.

(56) References Cited

U.S. PATENT DOCUMENTS

| | | | |
|---|---|---|---|
| 8,000,906 B2 * | 8/2011 | Henry et al. | 702/45 |
| 2009/0165567 A1 * | 7/2009 | Tombs | 73/861.355 |
| 2012/0059601 A1 * | 3/2012 | Kitami et al. | 702/45 |

* cited by examiner

*Primary Examiner* — Elias Desta
(74) *Attorney, Agent, or Firm* — Wenderoth, Lind & Ponack, L.L.P.

(57) ABSTRACT

A signal processing method for a Coriolis flowmeter including: performing frequency conversion to combine an oscillation frequency to each of two flow rate signals obtained by A/D conversion on input signals of the phase difference and/or the vibration frequency proportional to the Coriolis force acting on the at least one flow tube; measuring a frequency of a composite waveform associated with at least one of the vibration detection sensors; transmitting a control signal based on the measured frequency; controlling so that a sum frequency component or a difference frequency component of a composite component of a composite frequency signal is constant; and measuring phases from a sum signal or a difference signal of each of controlled converted composite frequencies, to thereby obtain a phase difference signal component.

17 Claims, 17 Drawing Sheets

FIG. 9
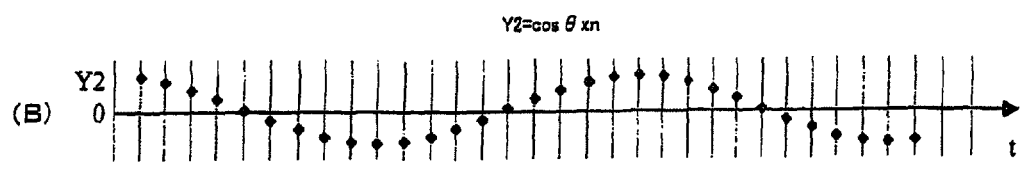
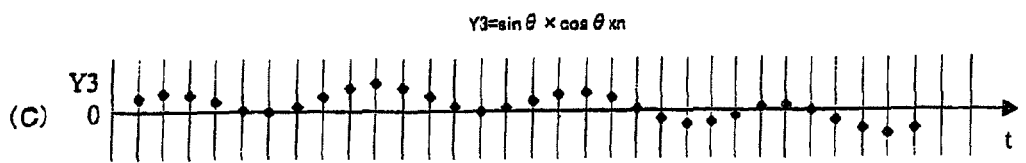
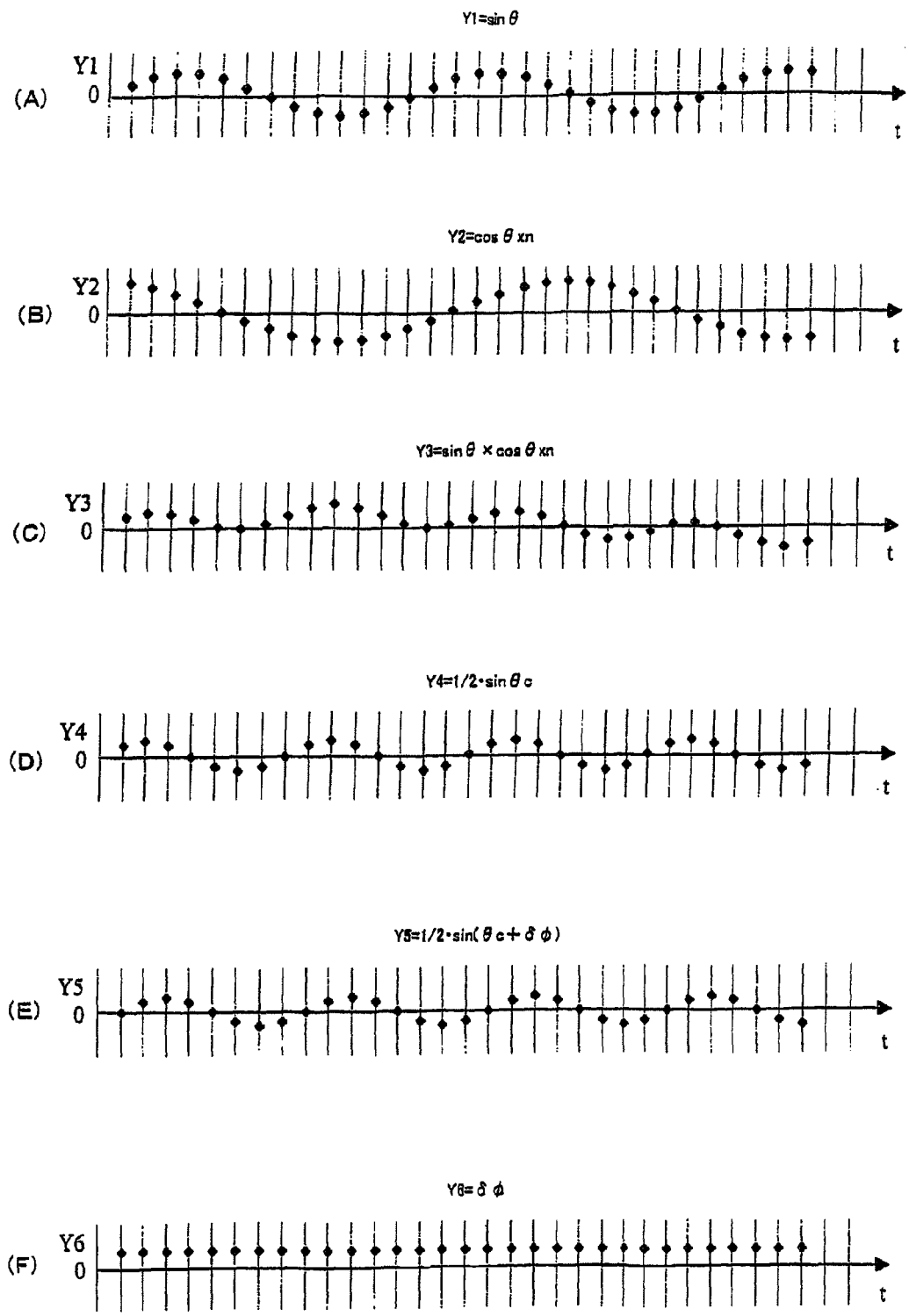
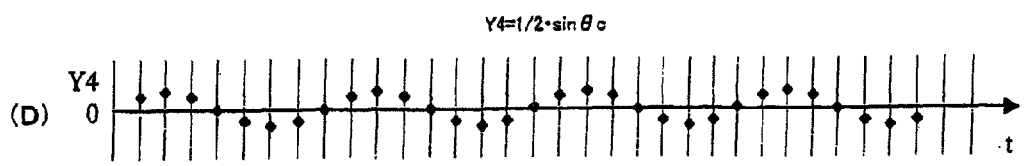
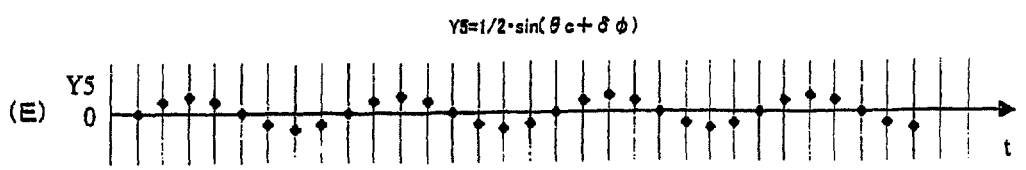
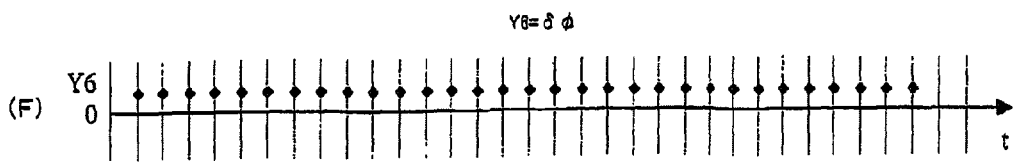

SIGNAL PROCESSING METHOD, SIGNAL PROCESSING APPARATUS, AND CORIOLIS FLOWMETER

TECHNICAL FIELD

The present invention relates to a Coriolis flowmeter for detecting a phase difference and/or a vibration frequency proportional to a Coriolis force acting on a flow tube to obtain a mass flow rate and/or density of a fluid to be measured.

BACKGROUND ART

In order to measure a density of an unknown fluid, it has been known to use a Coriolis flowmeter.

The Coriolis flowmeter is used to measure a mass flow rate based on the fact that a Coriolis force acting on a flow tube (hereinafter, flow tube to be vibrated is referred to as flow tube) is proportional to the mass flow rate in a case where the flow tube through which a fluid to be measured flows is supported at both ends and vibration is applied about a support point in a direction perpendicular to a flow direction of the flow tube.

In contrast to this, a vibration type density meter is used to measure a density of a fluid to be measured based on the fact that a resonance frequency of a flow tube (hereinafter, flow tube to be vibrated is referred to as flow tube) through which a fluid flows changes depending on a change in density.

Such a vibration type density meter has a principal structure common to the Coriolis flowmeter. Therefore, conventionally, a structure including the Coriolis flowmeter for measuring the mass flow rate of the fluid to be measured has been used to simultaneously measure the mass flow rate and the density.

Thus, when the cycle or frequency at which the flow tube is resonance-vibrated is measured, the density of the fluid may be measured. A shape of the flow tube is broadly divided into a straight-tube type and a curved-tube type.

When the curved-tube-type flow tube is used, the flow tube through which the fluid to be measured flows is supported at both ends and a central portion of the supported flow tube is alternately driven in a direction perpendicular to a support line, to measure a mass flow rate in symmetrical positions between both end support portions and the central portion of the flow tube.

When an alternate driving frequency of the flow tube is made equal to the natural frequency of the flow tube, a constant driving frequency corresponding to the density of the fluid to be measured is obtained, and hence the flow tube may be driven with small driving energy. Therefore, the flow tube is generally driven at the natural frequency.

When the density is to be measured using the curved-tube-type flow tube as described above, a combination of a coil and a magnet are generally used as a driving means for driving the flow tube.

The coil and the magnet are preferably attached to positions which are not offset in the vibration direction of the flow tube because a positional relationship deviation between the coil and the magnet is minimized. Therefore, in a case of a curved-tube-type Coriolis flowmeter including two parallel flow tubes, the two parallel flow tubes are attached so as to sandwich the coil and the magnet. Therefore, a design is made so that the two opposed flow tubes are separated from each other at an interval to sandwich at least the coil and the magnet.

Of Coriolis flowmeters including two flow tubes located in parallel planes, a Coriolis flowmeter having a large diameter or a Coriolis flowmeter having high flow tube rigidity is required to increase power of driving means, and hence it is necessary to sandwich large driving means between the two flow tubes. Therefore, a design is made so that an interval between the flow tubes is necessarily widened even in a fixed end portion which is a base portion of the flow tubes.

As illustrated in FIG. 13, a Coriolis flowmeter 1 which is generally known and includes U-shaped measurement tubes includes a detector 4 for two U-shaped measurement tubes 2 and 3, and a converter 5.

The detector 4 for the measurement tubes 2 and 3 includes a vibrator 6 for resonance-vibrating the measurement tubes 2 and 3, a left velocity sensor 7 for detecting a vibration velocity generated on a left side of the measurement tubes 2 and 3 vibrated by the vibrator 6, a right velocity sensor 8 for detecting a vibration velocity generated on a right side of the measurement tubes 2 and 3 vibrated by the vibrator 6, and a temperature sensor 9 for detecting a temperature of a fluid to be measured, which flows through the measurement tubes 2 and 3 at the detection of the vibration velocity. The vibrator 6, the left velocity sensor 7, the right velocity sensor 8, and the temperature sensor 9 are connected to the converter 5.

The fluid to be measured, which flows through the measurement tubes 2 and 3 of the Coriolis flowmeter 1, flows from the right side of the measurement tubes 2 and 3 (side on which right velocity sensor 8 is provided) to the left side thereof (side on which left velocity sensor 7 is provided).

Therefore, a velocity signal detected by the right velocity sensor 8 is an inlet-side velocity signal of the fluid to be measured flowing into the measurement tubes 2 and 3. A velocity signal detected by the left velocity sensor 7 is an outlet-side velocity signal of the fluid to be measured flowing from the measurement tubes 2 and 3.

The converter 5 of the Coriolis flowmeter includes a drive control section 10, a phase measurement section 11, and a temperature measurement section 12.

The converter 5 of the Coriolis flowmeter has a block structure as illustrated in FIG. 14.

That is, the converter 5 of the Coriolis flowmeter has an input and output port 15. A drive signal output terminal 16 included in the drive control section 10 is provided in the input and output port 15. The drive control section 10 outputs a predetermined mode signal, from the drive signal output terminal 16 to the vibrator 6 attached to the measurement tubes 2 and 3 to resonance-vibrate the measurement tubes 2 and 3.

Each of the left velocity sensor 7 and the right velocity sensor 8 which detect the vibration velocities may be an acceleration sensor.

The drive signal output terminal 16 is connected to a drive circuit 18 through an amplifier 17. The drive circuit 18 generates a drive signal for resonance-vibrating the measurement tubes 2 and 3 and outputs the drive signal to the amplifier 17. The amplifier amplifies the input drive signal and outputs the drive signal to the drive signal output terminal 16. The drive signal output from the amplifier 17 is output from the drive signal output terminal 16 to the vibrator 6.

A left velocity signal input terminal 19 to which a detection signal of the vibration velocity generated on the left side of the measurement tubes 2 and 3 vibrated by the vibrator 6 is input is provided in the input and output port 15. The left velocity signal input terminal 19 is included in the phase measurement section 11.

A right velocity signal input terminal 20 to which a detection signal of the vibration velocity generated on the right side of the measurement tubes 2 and 3 vibrated by the vibrator 6 is input is provided in the input and output port 15. The right velocity signal input terminal 20 is included in the phase measurement section 11.

The phase measurement section 11 performs A/D conversion on the vibration signals of the pair of velocity sensors in the case where the predetermined mode signal is output from the drive signal output terminal 16 to the vibrator 6 attached to the measurement tubes 2 and 3 to vibrate the measurement tubes 2 and 3 by the vibrator 6, to thereby perform digital conversion processing, and then obtains a phase difference between the converted signals.

The left velocity signal input terminal 19 is connected to an input terminal of an amplifier 21. An output terminal of the amplifier 21 is connected to an A/D converter 22. The A/D converter 22 converts, into a digital value, an analog signal obtained by amplifying the vibration signal output from the left velocity signal input terminal 19 by the amplifier 21.

The A/D converter 22 is connected to a computing device 23.

Further, the right velocity signal input terminal 20 is connected to an input terminal of an amplifier 24. An output terminal of the amplifier 24 is connected to an A/D converter 25. The A/D converter 25 converts, into a digital value, an analog signal obtained by amplifying the vibration signal output from the right velocity signal input terminal 20 by the amplifier 24.

Further, the digital signal output from the A/D converter 25 is input to the computing device 23.

Further, a temperature signal input terminal 26 included in the temperature measurement section 11 to which a detection value from the temperature sensor 9 is input is provided in the input and output port 15. The temperature measurement section 11 performs tube temperature compensation based on the detection temperature obtained by the temperature sensor 9 which is provided in the measurement tubes 2 and 3 and detects an internal temperature of the measurement tubes 2 and 3.

A resistance type temperature sensor is generally used as the temperature sensor 9 to measure a resistance value, to thereby calculate a temperature.

The temperature signal input terminal 26 is connected to a temperature measurement circuit 27. The temperature measurement circuit 27 calculates the internal temperature of the measurement tubes 2 and 3 based on the resistance value output from the temperature sensor 9. The internal temperature of the measurement tubes 2 and 3 which is calculated by the temperature measurement circuit 27 is input to the computing device 23.

In the phase measurement method using the Coriolis flowmeter 1 as described above, vibration is applied in a primary mode, to the measurement tubes 2 and 3, from the vibrator 6 attached to the measurement tubes 2 and 3. When the fluid to be measured flows into the measurement tubes 2 and 3 while the vibration is applied, a phase mode is produced in the measurement tubes 2 and 3.

Therefore, the signal (inlet-side velocity signal) from the right velocity sensor 8 and the signal (outlet-side velocity signal) from the left velocity sensor 7 in the Coriolis flowmeter 1 are output as a form in which the two signals are superimposed on each other. A signal output as the form in which the two signals are superimposed on each other includes not only a flow rate signal but also a large number of unnecessary noise components. In addition, a frequency is changed depending on, for example, a change in density of the fluid to be measured.

Therefore, it is necessary to remove an unnecessary signal from the signals from the right velocity sensor 8 and the left velocity sensor 7. However, it is very difficult to remove the unnecessary signal from the signals from the right velocity sensor 8 and the left velocity sensor 7 to calculate the phase.

Further, the Coriolis flowmeter 1 is often required to have very-high-precision measurement and high-speed response. In order to satisfy such requirements, a computing device having very-complex computation and high-processing performance is necessary, and hence the Coriolis flowmeter 1 itself is very expensive.

Thus, the Coriolis flowmeter 1 requires an established phase difference measurement method using both an optimum filter always fit to a measurement frequency and a high-speed computing method.

In conventional phase difference measurement methods of calculating a flow rate, a filter processing method of removing noise is divided into a method using an analog filter and a method using a digital filter.

The method using the analog filter may be relatively inexpensive (see, for example, Patent Document 1 and Patent Document 2). However, Patent Document 1 and Patent Document 2 have a limit to improve the performance of the filter, and hence, there is a problem that the filter is not sufficient for the Coriolis flowmeter.

In recent years, a large number of Coriolis flowmeters using digital signal processing have been developed, and the method using the digital filter has been developed as the filter processing method of removing noise in the conventional phase difference measurement methods of calculating the flow rate.

Examples of conventional types of the Coriolis flowmeters using digital signal processing include a method of measuring a phase using a Fourier transform (see, for example, Patent Document 3) and a method of selecting an optimum table fit to an input frequency from filter tables including a notch filter and a band-pass filter to measure a phase (see, for example, Patent Document 4 and Patent Document 5).

<<Phase Measurement Method Using Fourier Transform>>

A converter of the Coriolis flowmeter based on the phase measurement method using the Fourier transform has a block structure as illustrated in FIG. 15.

In FIG. 15, the left velocity signal input terminal 19 provided in the input and output port 15 to which the detection signal of the vibration velocity (outlet-side velocity signal) which is generated on the left side of the measurement tubes 2 and 3 vibrated by the vibrator 6 and which is detected by the left velocity sensor 7 is input is connected to a low-pass filter 30. The low-pass filter 30 is a circuit for extracting, through a frequency filter, only a low-frequency left velocity signal (outlet-side velocity signal) from the left velocity signal (outlet-side velocity signal) output from the left velocity sensor 7 detecting the vibration velocity generated on the left side of the measurement tubes 2 and 3 in the case where the measurement tubes 2 and 3 are vibrated by the vibrator 6.

The low-pass filter 30 is connected to an A/D converter 31. The A/D converter 31 converts, into a digital signal, the left velocity signal which is the analog signal output from the low-pass filter 30. The left velocity signal obtained as the digital signal by conversion by the A/D converter 31 is input to a phase difference measurement unit 32.

The A/D converter 31 is connected to a timing generator 33. The timing generator 33 generates a timing of sampling M-times (M is natural number) the input frequency.

On the other hand, the right velocity signal input terminal 20 provided in the input and output port 15 to which the detection signal of the vibration velocity (inlet-side velocity signal) which is generated on the right side of the measurement tubes 2 and 3 vibrated by the vibrator 6 and which is detected by the right velocity sensor 8 is input is connected to a low-pass filter 34. The low-pass filter 34 is a circuit for extracting, through a frequency filter, only a low-frequency right velocity signal (inlet-side velocity signal) from the right velocity signal (inlet-side velocity signal) output from the right velocity sensor 8 detecting the vibration velocity generated on the right side of the measurement tubes 2 and 3 in the case where the measurement tubes 2 and 3 are vibrated by the vibrator 6.

The low-pass filter 34 is connected to an A/D converter 35. The A/D converter 35 converts, into a digital signal, the right velocity signal which is the analog signal output from the low-pass filter 34. The right velocity signal obtained as the digital signal by conversion by the A/D converter 35 is input to the phase difference measurement unit 32.

Further, the A/D converter 35 is connected to the timing generator 33. The timing generator 33 generates a timing of sampling M-times (M is natural number) the input frequency.

Further, the right velocity signal input terminal 20 provided in the input and output port 15 to which the detection signal of the vibration velocity (inlet-side velocity signal) which is generated on the right side of the measurement tubes 2 and 3 vibrated by the vibrator 6 and which is detected by the right velocity sensor 8 is input is connected to a frequency measurement unit 36. The frequency measurement unit 36 measures the frequency of the detection signal of the vibration velocity (inlet-side velocity signal) which is generated on the right side of the measurement tubes 2 and 3 vibrated by the vibrator 6 and which is detected by the right velocity sensor 8.

The frequency measurement unit 36 is connected to the timing generator 33. The frequency measured by the frequency measurement unit 36 is output to the timing generator 33. The timing of sampling M-times (M is natural number) the input frequency is generated by the timing generator 33 and output to the A/D converters 31 and 35.

The phase difference measurement unit 32, the timing generator 33, and the frequency measurement unit 36 are included in a phase measurement computing device 40.

In the phase measurement method using the Fourier transform as illustrated in FIG. 15, the input signal (inlet-side velocity signal) from the right velocity sensor 8 is first input to the frequency measurement unit 36 to measure a frequency. The frequency measured by the frequency measurement unit 36 is input to the timing generator 33. The timing of sampling M-times (M is natural number) the input frequency is generated by the timing generator 33 and input to the A/D converters 31 and 35.

Further, the detection signal of the vibration velocity (outlet-side velocity signal) which is generated on the left side of the measurement tubes 2 and 3 and obtained as the digital signal by conversion by the A/D converter 31 and the detection signal of the vibration velocity (inlet-side velocity signal) which is generated on the right side of the measurement tubes 2 and 3 and obtained as the digital signal by conversion by the A/D converter 35 are input to the phase difference measurement unit 32. The detection signals are Fourier-transformed by a discrete Fourier transform unit incorporated in the phase difference measurement unit 32 and a phase difference is computed based on a ratio between a real component and imaginary component of the converted signals.

<<Phase Measurement Method Using Digital Filter>>

Converters of the Coriolis flowmeter based on the phase measurement method using the digital filter are described with reference to block structural diagrams illustrated in FIGS. 16 and 17.

Frequency selection means such as a notch filter or a band-pass filter is used as the digital filter. An S/N ratio of an input signal is improved using the frequency selection means such as the notch filter or the band-pass filter.

FIG. 16 illustrates a block structure of a converter of the Coriolis flowmeter using the notch filter as the digital filter.

The input and output port 15, the left velocity signal input terminal 19, the right velocity signal input terminal 20, the low-pass filters 30 and 34, and the A/D converters 31 and 35 as illustrated in FIG. 16 have the same structures as the input and output port 15, the left velocity signal input terminal 19, the right velocity signal input terminal 20, the low-pass filters 30 and 34, and the A/D converters 31 and 35 as illustrated in FIG. 15, respectively.

In FIG. 16, the A/D converter 31 is connected to a notch filter 51. The notch filter 51 selects a frequency based on the left velocity signal which is obtained as the digital signal by conversion by the A/D converter 31, so as to improve an S/N ratio of an input signal to be output.

The notch filter 51 is connected to a phase measurement unit 52. The phase measurement unit 52 measures a phase of the left velocity signal which is obtained as the digital signal by conversion and which is improved in S/N ratio by the notch filter 51.

Further, the notch filter 51 is connected to a frequency measurement unit 53. The frequency measurement unit 53 measures a frequency of the left velocity signal which is obtained as the digital signal by conversion and which is improved in S/N ratio by the notch filter 51.

The frequency measured by the frequency measurement unit 53 is input to the notch filter 51.

Further, the A/D converter 35 is connected to a notch filter 54. The notch filter 54 selects a frequency based on the left velocity signal which is obtained as the digital signal by conversion by the A/D converter 31, so as to improve an S/N ratio of an input signal to be output.

The notch filter 54 is connected to the phase measurement unit 52. The phase measurement unit 52 measures a phase of the right velocity signal which is obtained as the digital signal by conversion and which is improved in S/N ratio by the notch filter 54.

Further, the frequency measured by the frequency measurement unit 53 is input to the notch filter 54.

In FIG. 16, a clock 55 is used for synchronization, and input to the A/D converters 31 and 35 to synchronize the A/D converter 31 and the A/D converter 35 with each other.

The notch filters 51 and 54, the phase difference measurement unit 52, the frequency measurement unit 53, and the clock 55 are included in a phase measurement computing device 50.

FIG. 17 illustrates a block structure of a converter of the Coriolis flowmeter using the band-pass filter (BPF) as the digital filter.

The input and output port 15, the left velocity signal input terminal 19, the right velocity signal input terminal 20, the low-pass filters 30 and 34, and the A/D converters 31 and 35 as illustrated in FIG. 17 have the same structures as the input and output port 15, the left velocity signal input terminal 19, the right velocity signal input terminal 20, the low-pass filters 30 and 34, and the A/D converters 31 and 35 as illustrated in FIG. 16, respectively.

In FIG. 17, the A/D converter 31 is connected to a band-pass filter (BPF) 61. The band-pass filter 61 is a circuit for extracting, through a frequency filter, only a left velocity signal having a set frequency (outlet-side velocity signal) from the left velocity signal (outlet-side velocity signal) which is output from the left velocity sensor 7 detecting the vibration velocity generated on the left side of the measurement tubes 2 and 3 and which is obtained as the digital signal by conversion by the A/D converter 31 in the case where the measurement tubes 2 and 3 are vibrated by the vibrator 6.

The band-pass filter 61 is connected to a phase measurement unit 62. The phase measurement unit 62 measures a phase of the left velocity signal which is obtained as the digital signal by conversion and which is improved in S/N ratio by the band-pass filter 61.

Further, the band-pass filter 61 is connected to a frequency measurement unit 63. The frequency measurement unit 63 measures a frequency of the left velocity signal which is obtained as the digital signal by conversion by the A/D converter 31 and which is improved in S/N ratio by the band-pass filter 61.

The frequency measured by the frequency measurement unit 63 is input to the band-pass filter 61.

Further, the A/D converter 35 is connected to a band-pass filter 64. The band-pass filter 64 is a circuit for extracting, through a frequency filter, only a right velocity signal having a set frequency (inlet-side velocity signal) from the right velocity signal (inlet-side velocity signal) which is output from the right velocity sensor 8 detecting the vibration velocity generated on the right side of the measurement tubes 2 and 3 and which is obtained as the digital signal by conversion by the A/D converter 35 in the case where the measurement tubes 2 and 3 are vibrated by the vibrator 6.

The band-pass filter 64 is connected to the phase measurement unit 62. The phase measurement unit 62 measures a phase of the left velocity signal which is obtained as the digital signal by conversion and which is improved in S/N ratio by the band-pass filter 64.

The band-pass filter 64 is connected to the frequency measurement unit 63. The frequency measured by the frequency measurement unit 63 is input to the band-pass filter 64.

In FIG. 17, a clock 65 is used for synchronization, and a clock signal from the clock 65 is input to the A/D converters 31 and 35 to synchronize the A/D converter 31 and the A/D converter 35 with each other.

The band-pass filters 61 and 64, the phase measurement unit 62, the frequency measurement unit 63, and the clock 65 are included in a phase measurement computing device 60.

PRIOR ART DOCUMENT

Patent Document

[Patent Document 1] JP 02-66410 A
[Patent Document 2] JP 10-503017 A
[Patent Document 3] JP 2799243 B
[Patent Document 4] JP 2930430 B
[Patent Document 5] JP 3219122 B

SUMMARY OF THE INVENTION

Problems to be solved by the Invention

In the phase measurement method using the Fourier transform as described in Patent Document 3, when the input frequency of the input detection signal of the vibration velocity is constant, a phase measurement method having very-high-frequency selectivity may be performed because the Fourier transform is used for frequency selection.

However, in the method using the Fourier transform as described in Patent Document 3, when the input frequency of the input detection signal of the vibration velocity is changed according to a density or a temperature, it is necessary to change the transform method or the sampling rate. Therefore, the computing cycle or the computing method is changed, and hence a measurement value is varied and thus unstabilized.

In addition, in the method using the Fourier transform as described in Patent Document 3, when the input frequency of the input detection signal of the vibration velocity is changed according to the density or the temperature, it is necessary to accurately synchronize the sampling rate with the input frequency of the input vibration velocity signal, and hence a design is very complicated.

Therefore, there is a problem that, when the temperature of the fluid to be measured is rapidly changed or the density is rapidly changed by mixing air bubbles into the fluid, the measurement precision is extremely reduced.

Further, the method using the Fourier transform as described in Patent Document 3 has a problem that the number of computing processings becomes very large because of the execution of the Fourier transform.

In the methods of selecting the optimum table fit to the input frequency from the filter tables including the notch filter and the band-pass filter to measure the phase as described in Patent Document 4 and Patent Document 5, when the sampling rate is held, the design may be simplified.

However, as in the method using the Fourier transform as described in Patent Document 3, the phase measurement methods using the digital filter as described in Patent Document 4 and Patent Document 5 require a very large number of filter tables corresponding to changed input frequencies, and hence have a problem that memory consumption of a computing device is large.

In addition, the phase measurement methods using the digital filter as described in Patent Document 4 and Patent Document 5 have a problem that it is difficult to select the optimum filter in a case where the input frequency rapidly changes.

Further, the phase measurement methods using the digital filter as described in Patent Document 4 and Patent Document 5 have a problem that a vary large number of computations as required to improve frequency selection performance.

The phase measurement methods using the digital filter as described in Patent Document 4 and Patent Document 5 have the following problems.

(1) The method cannot follow the change in input frequency at high precision. That is, it is very difficult to realize measurement in a case where the density of the fluid to be measured rapidly changes because of air bubble mixing.

(2) In order to improve the frequency selection performance, a very large number of computations are required. Therefore, it is difficult to realize high-speed response, and hence the method is unsuitable for batch processing for a short period of time.

(3) The memory consumption of the computing device is large, and hence the design is complicated. Therefore, a circuit structure and design are complicated and very disadvantageous in cost.

When all the factors are considered, in any of the conventional phase measurement methods including the digital filter processing, a noise of a frequency band other than the tube frequencies of the measurement tubes 2 and 3 is removed, and hence the switching of the filter table, the change of the computing method, and the change of the sampling rate are required to always follow the tube frequencies of the measurement tubes 2 and 3. Therefore, there is a problem that it is necessary to perform computation which is very complicated and lacks high-speed performance.

Thus, when the measurement tubes 2 and 3 are vibrated by the vibrator 6, it is very likely to generate a computing error in each variation of the input frequencies of the vibration velocity signals which are detected by the right velocity sensor 8 for detecting the vibration velocity generated on the right side of the measurement tubes 2 and 3 and the left velocity sensor 7 for detecting the vibration velocity generated on the left side of the measurement tubes 2 and 3, and hence there is a problem that measurement precision is very low.

An object of the present invention is to provide a signal processing method, a signal processing apparatus, and a Coriolis flowmeter, in which even when a temperature of a fluid to be measured changes, even when air bubbles are mixed into the fluid to be measured, or even when the fluid to be measured rapidly changes from a gas to a liquid, measurement may be always performed with constant precision, phase and frequency measurements with high filtering performance are realized, and a computing processing amount may be reduced to an extremely small amount.

Means for solving the Problems

In order to solve the above-mentioned problems, according to a first aspect of the present invention, a signal processing method for a Coriolis flowmeter in which at least one flow tube or a pair of flow tubes which is included in a measurement flow tube is alternately driven by causing a vibrator to be actuated by a driving device to vibrate the at least one flow tube or the pair of flow tubes, and at least one of a phase difference and a vibration frequency proportional to a Coriolis force acting on the at least one flow tube or the pair of flow tubes is detected by two velocity sensors or acceleration sensors which are vibration detection sensors, to thereby obtain at least one of a mass flow rate and a density of a fluid to be measured, includes:

performing frequency conversion to combine, based on an arbitrary oscillation frequency, each of two flow rate signals obtained by A/D conversion on input signals of the vibration frequency proportional to the Coriolis force acting on the at least one flow tube or the pair of flow tubes, which are detected by the two velocity sensors or acceleration sensors, to obtain a composite frequency signal;

measuring a frequency of the composite frequency signal associated with at least one of the two velocity sensors or acceleration sensors;

transmitting a control signal based on the measured frequency;

controlling a frequency of a sum or difference frequency component of the composite frequency signal to a constant value;

obtaining a resonance frequency of the at least one flow tube or the pair of flow tubes based on the control signal, calculating the density of the fluid to be measured based on the control signal; and measuring a phase from the sum or difference frequency component of the composite frequency signal having the controlled frequency.

In order to solve the above-mentioned problems, according to a second aspect of the present invention, in the signal processing method according to the first aspect, the frequency conversion for combining based on the arbitrary oscillation frequency includes:

multiplying an input signal SIN $\theta_1$ from the one of the two velocity sensors or acceleration sensors by the transmitted control signal cos $\theta_2$; and filtering an output signal obtained by the multiplying by a frequency filter to extract only a low-frequency signal.

In order to solve the above-mentioned problems, according to a third aspect of the present invention, in the signal processing method according to the first aspect, the frequency conversion for combining based on the arbitrary oscillation frequency includes:

multiplying an input signal SIN $\theta_1$ from the one of the two velocity sensors or acceleration sensors by the transmitted control signal cos $\theta_2$; and filtering an output signal obtained by the multiplying by a frequency filter to extract only a high-frequency signal.

In order to solve the above-mentioned problems, according to a fourth aspect of the present invention, in the signal processing method according to the first aspect:

the input signals of the vibration frequency proportional to the Coriolis force acting on the at least one flow tube or the pair of flow tubes, which are detected by the two velocity sensors or acceleration sensors, are sampled by the A/D conversion to obtain digital signals; and the composite frequency signal obtained by the frequency conversion based on the transmitted control signal is controlled so that the frequency of the sum or difference frequency component of the composite frequency signal is ¼ of a sampling frequency for the A/D conversion.

In order to solve the above-mentioned problems, according to a fifth aspect of the present invention, a signal processing apparatus for a Coriolis flowmeter in which at least one flow tube or a pair of flow tubes which is included in a measurement flow tube is alternately driven by causing a vibrator to be actuated by a driving device to vibrate the at least one flow tube or the pair of flow tubes, and at least one of a phase difference and a vibration frequency proportional to a Coriolis force acting on the at least one flow tube or the pair of flow tubes is detected by a velocity sensor or acceleration sensor which is a vibration detection sensor, to thereby obtain at least one of a mass flow rate and a density of a fluid to be measured, includes:

a transmitter 90 for transmitting a frequency signal which is modulatable;

a frequency converter 85 for performing frequency conversion to add (or subtract) an output frequency $F_x$ from the transmitter 90 to (or from) an input frequency of an input signal detected by the velocity sensor or acceleration sensor and shifting a frequency value obtained by the frequency conversion to a constant value; and a phase difference measurement section for measuring a phase difference of the converted frequency signal output from the frequency converter 85.

In order to solve the above-mentioned problems, according to a sixth aspect of the present invention, a signal processing apparatus for a Coriolis flowmeter in which at least one flow tube or a pair of flow tubes which is included in a measurement flow tube is alternately driven by causing a vibrator to be actuated by a driving device to vibrate the at least one flow tube or the pair of flow tubes, and at least one of a phase difference and a vibration frequency proportional to a Coriolis force acting on the at least one flow tube or the pair of flow tubes is detected by a pair of velocity sensors or acceleration sensors which are a pair of vibration detection sensors, to thereby obtain at least one of a mass flow rate and a density of a fluid to be measured, includes:

a transmitter 120 for transmitting a frequency signal which is modulatable;

a first frequency conversion section 110 for performing frequency conversion to add (or subtract) an output frequency $\theta_{X_n}$ from the transmitter 120 to (or from) an input signal frequency $\theta$ obtained by converting a signal of one of the pair of vibration detection sensors into a digital signal by a first A/D converter 31, to adjust a frequency value obtained by the frequency conversion to a constant value; and a second frequency conversion section 140 for performing frequency conversion to add (or subtract) the output frequency $\theta_{Xn}$ from the transmitter 120 to (or from) an input signal frequency $\theta$ obtained by converting a signal of another one of the pair of vibration detection sensors into a digital signal by a second A/D converter 35, to adjust a frequency value obtained by the frequency conversion to a constant value.

In order to solve the above-mentioned problems, according to a seventh aspect of the present invention, a signal processing apparatus for a Coriolis flowmeter in which at least one flow tube or a pair of flow tubes which is included in a measurement flow tube is alternately driven by causing a vibrator to be actuated by a driving device to vibrate the at least one flow tube or the pair of flow tubes, and at least one of a phase difference and a vibration frequency proportional to a Coriolis force acting on the at least one flow tube or the pair of flow tubes is detected by a pair of vibration detection sensors, to thereby obtain at least one of a mass flow rate and a density of a fluid to be measured, includes:

a transmitter 120 for transmitting a frequency signal which is modulatable;

a first frequency conversion section 110 for shifting in frequency, to a predetermined constant frequency signal, an input signal frequency $\theta$ obtained by converting a signal of one velocity sensor of the pair of vibration detection sensors into a digital signal by a first A/D converter 31, based on an output frequency $\theta_{Xn}$ from the transmitter 120 to move the input signal frequency to a desired frequency band;

a second frequency conversion section 140 for shifting in frequency, to a constant frequency signal, an input signal frequency $\theta$ obtained by converting a signal of another velocity sensor of the pair of vibration detection sensors into a digital signal by a second A/D converter 35, based on the output frequency $\theta_{Xn}$ from the transmitter 120 to move the input signal frequency to a desired frequency band; and a frequency measurement section 160 for measuring a frequency of a first frequency signal, which is obtained as the predetermined constant frequency signal through the shifting by and output from the first frequency conversion section 110, and outputting the measured frequency of the first frequency signal to the transmitter 120 to control, based on the frequency after the shifting by the first frequency conversion section 110, output frequencies from the first frequency conversion section and the second frequency conversion section so that the input signal frequency obtained by converting the signal of the one velocity sensor of the pair of vibration detection sensors into the digital signal by the first A/D converter 31 is a desired frequency.

In order to solve the above-mentioned problems, according to an eighth aspect of the present invention, in the signal processing apparatus according to any one of the fifth, sixth, and seventh aspects, the frequency conversion section 110 includes:

a multiplier 111 for multiplying a reference signal $\cos\theta_2$ from the transmitter 120 by an input signal $\mathrm{SIN}\,\theta_1$ from the first A/D converter 31; and a low-pass filter 112 for filtering an output signal obtained by the multiplication by the multiplier 111 through a frequency filter to extract only a low-frequency signal.

In order to solve the above-mentioned problems, according to a ninth aspect of the present invention, in the signal processing apparatus according to any one of the fifth, sixth, and seventh aspects, the frequency conversion section 110 includes:

a multiplier 111 for multiplying a reference signal $\cos\theta_2$ from the transmitter 120 by an input signal $\mathrm{SIN}\,\theta_1$ from the first A/D converter 31; and a high-pass filter 112 for filtering an output signal obtained by the multiplication by the multiplier 111 through a frequency filter to extract only a high-frequency signal.

In order to solve the above-mentioned problems, according to a tenth aspect of the present invention, in the signal processing apparatus according to the seventh, eighth, and ninth aspects:

the frequency measurement section 160 includes a multiplier 161 connected to the first frequency conversion section 110, a low-pass filter 162 connected to the multiplier 161, and a transmitter 163 for frequency measurement which is connected to the low-pass filter 162 and receives an output signal from the low-pass filter 162;

the multiplier 161 compares an output signal $\sin(\theta+\theta_{Xn})$ from the frequency conversion section 110 with a phase of an output signal $\cos\delta$ from the transmitter 163 for frequency measurement and outputs a difference signal and a sum signal to the low-pass filter 162;

the low-pass filter 162 filters an output signal from the multiplier 161 through a frequency filter to extract only a low-frequency signal; and a phase amount V of a fundamental output waveform is generated based on the low-frequency signal output from the low-pass filter 162 and satisfies a condition of V=0 by the transmitter 163 for frequency measurement.

In order to solve the above-mentioned problems, according to an eleventh aspect of the present invention, the signal processing apparatus according to any one of the seventh, eighth, ninth, and tenth aspects further includes a clock for synchronizing an output of the first A/D converter 31 and an output of the second A/D converter 35 to synchronize a digital signal of one of the pair of vibration detection sensors which is output from the first A/D converter 31 and a digital signal of another one of the pair of vibration detection sensors which is output from the second A/D converter 35.

In order to solve the above-mentioned problems, according to a twelfth aspect of the present invention, in the signal processing apparatus according to any one of the seventh, eighth, ninth, tenth, and eleventh aspects, the phase measurement section performs processing of a discrete Fourier transform (DFT) or a fast Fourier transform (FFT).

In order to solve the above-mentioned problems, according to a thirteenth aspect of the present invention, a Coriolis flowmeter in which at least one flow tube or a pair of flow tubes which is included in a measurement flow tube is alternately driven by causing a vibrator to be actuated by a driving device to vibrate the at least one flow tube or the pair of flow tubes, and at least one of a phase difference and a vibration frequency proportional to a Coriolis force acting on the at least one flow tube or the pair of flow tubes is detected by a pair of velocity sensors or acceleration sensors which are a pair of vibration detection sensors, to thereby obtain at least one of a mass flow rate and a density of a fluid to be measured, includes:

a transmitter 120 for transmitting a frequency signal which is modulatable;

a first frequency conversion section 110 for shifting in frequency, to a predetermined constant frequency signal, an input signal frequency $\theta$ obtained by converting a signal of one velocity sensor of the pair of vibration detection sensors into a digital signal by a first A/D converter 31, based on an output frequency $\theta_{X_n}$ from the transmitter 120 to move the input signal frequency to a desired frequency band;

a second frequency conversion section 140 for shifting in frequency, to a predetermined constant frequency signal, an input signal frequency θ obtained by converting a signal of another velocity sensor of the pair of vibration detection sensors into a digital signal by a second A/D converter 35, based on the output frequency $\theta_{X_n}$ from the transmitter 120 to move the input signal frequency to a desired frequency band; and a frequency measurement section 160 for measuring a frequency of a first frequency signal, which is obtained as the predetermined constant frequency signal through the shifting by and output from the first frequency conversion section 110, and outputting the measured frequency of the first frequency signal to the transmitter 120 to control, based on the frequency after the shifting by the first frequency conversion section 110, output frequencies from the first frequency conversion section and the second frequency conversion section so that the input signal frequency obtained by converting the signal of the one velocity sensor of the pair of vibration detection sensors into the digital signal by the first A/D converter 31 is a desired frequency.

Examples of the flow tube of the Coriolis flowmeter include a curved tube and a straight tube. There is a type driven in any of various modes including a primary mode and a secondary mode, as a mode for driving the flow tube.

As is well known, the driving frequency band obtained from the flow tube is several ten Hz to several kHz. For example, when the flow tube using a U-shaped tube is vibrated in the primary mode, a frequency is approximately 100 Hz. When the flow tube having a straight shape is vibrated in the primary mode, a frequency in a range of approximately 500 Hz to 1,000 Hz is realized.

However, it is very difficult to perform the phase and frequency measurements of the Coriolis flowmeter by always the same processing over the frequency band of several ten Hz to several kHz in a single flowmeter converter. Therefore, it is necessary to separately design several types.

According to the signal processing method in the present invention, the essential problems as described above may be removed by advantageous signal processing based on an identification algorithm. Even in the case of the change in temperature of the fluid to be measured, the mixing of air bubbles, or the rapid change of the fluid to be measured from the gas to the liquid, the phase and frequency measurements may be always performed with constant precision, and hence high performance may be provided.

According to the signal processing apparatus in the present invention, even when the temperature of the fluid to be measured changes, even when the air bubbles are mixed into the fluid to be measured, or even when the fluid to be measured rapidly changes from the gas to the liquid, the measurement may be always performed with constant precision and the phase and frequency measurements may be performed with a small computing amount.

According to the Coriolis flowmeter in the present invention, even when the temperature of the fluid to be measured changes, even when the air bubbles are mixed into the fluid to be measured, or even when the fluid to be measured rapidly changes from the gas to the liquid, the measurement may be always performed with constant precision and the phase and frequency measurements may be performed with a small computing amount.

BRIEF DESCRIPTION OF THE DRAWINGS

FIG. 9 Diagrams illustrating time charts for the specific structure of the signal processing apparatus illustrated in FIG. 3.

MODES FOR CARRYING OUT THE INVENTION

The present invention has been made so as to achieve the object that measurement may be always performed with constant precision and an extremely small computing processing amount even when the temperature of the fluid to be measured changes, even when the air bubbles are mixed into the fluid to be measured, or even when the fluid to be measured rapidly changes from the gas to the liquid.

Embodiment 1

Hereinafter, Embodiment 1 of a mode for carrying out the present invention is described with reference to FIGS. 1 to 9.

Figure 1:
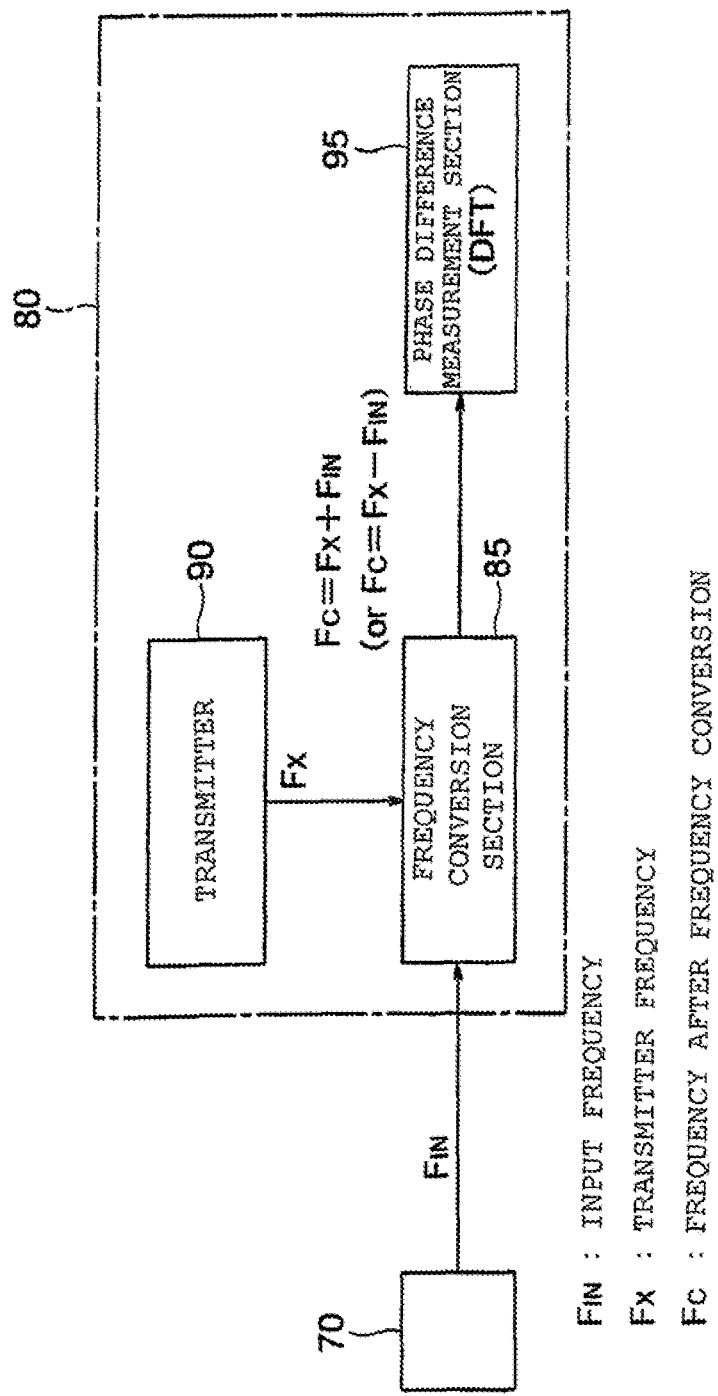
FIG. 1 A block diagram illustrating a principle of a signal processing apparatus according to the present invention.
Figure 2:
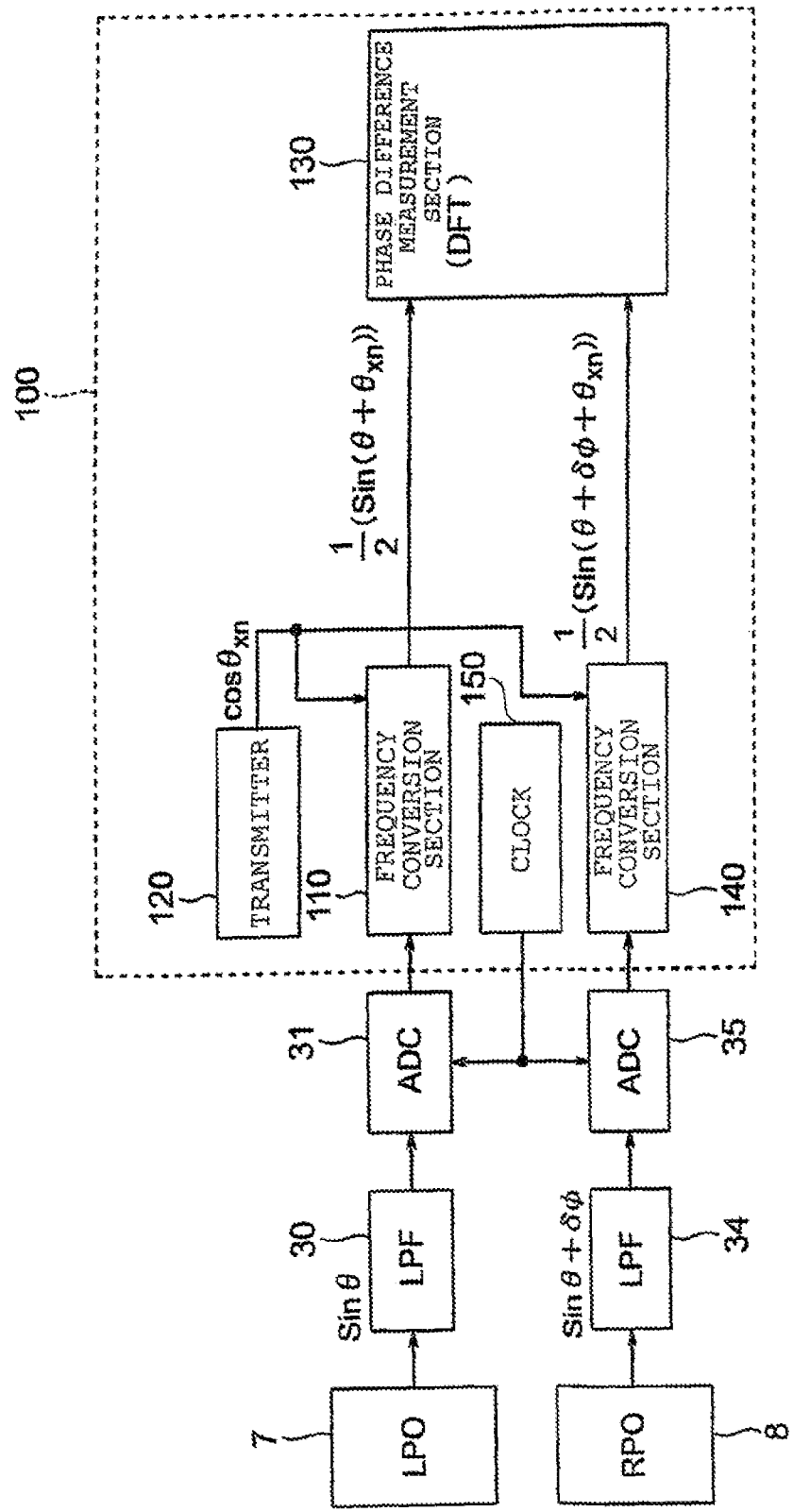
FIG. 2 A block diagram illustrating a specific structure of the signal processing apparatus illustrated in FIG. 1.
Figure 3:
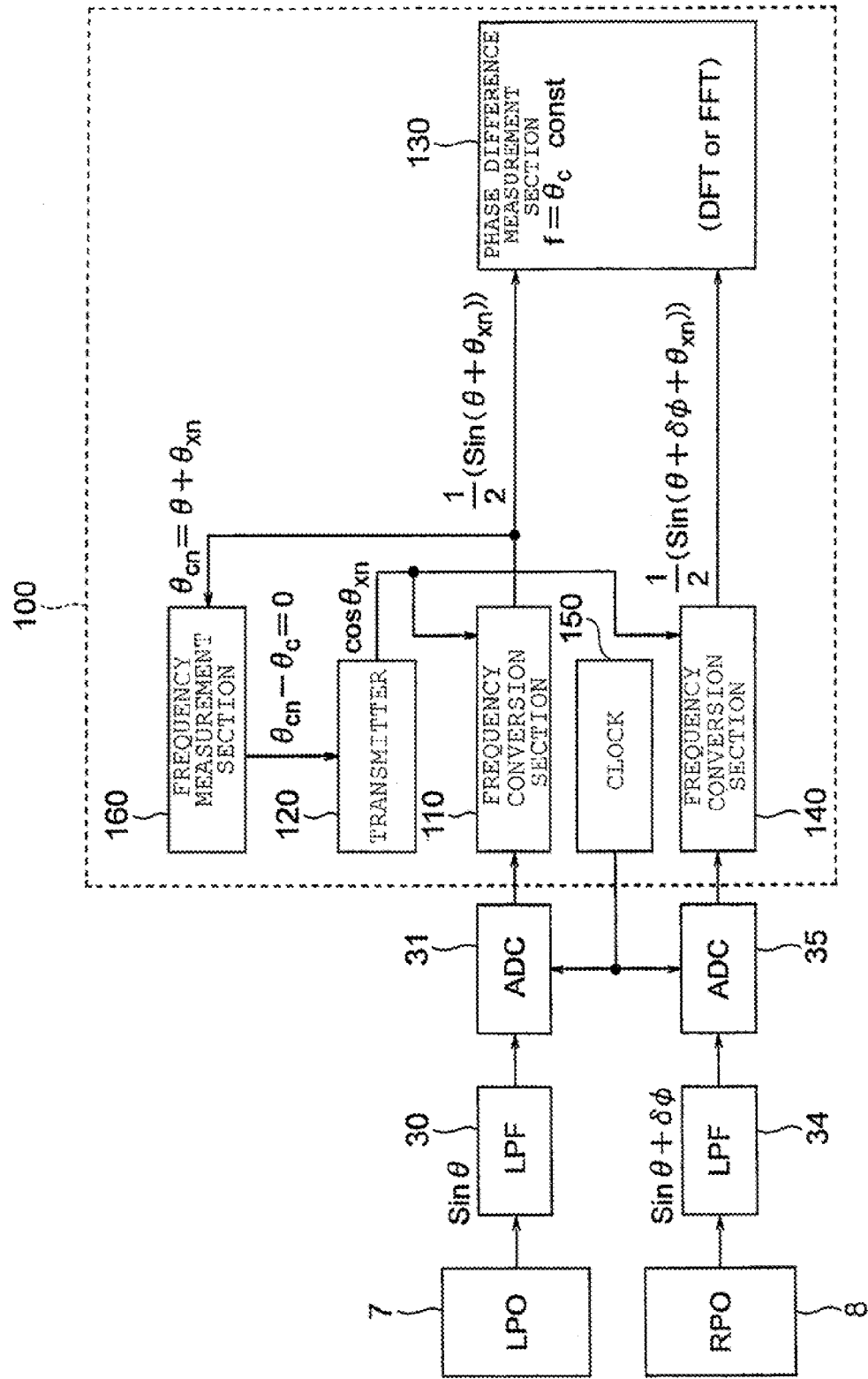
FIG. 3 A block diagram illustrating a specific structure of the signal processing apparatus illustrated in FIG. 2 using a feedback control method.
Figure 4:
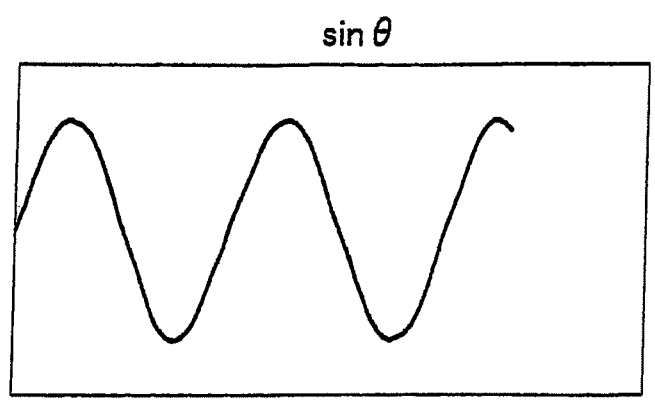
FIG. 4 A diagram illustrating an output signal from an LPF illustrated in FIG. 3.
Figure 5:
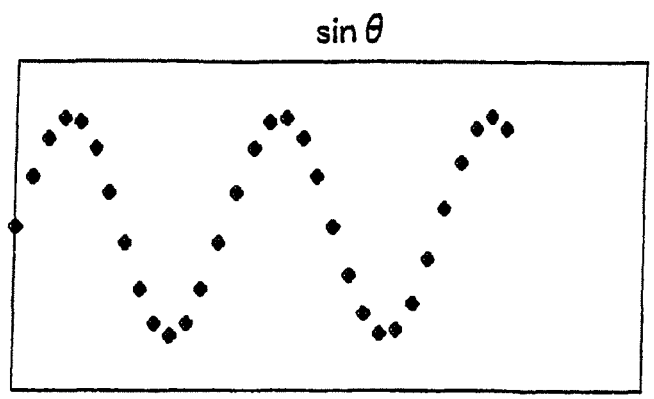
FIG. 5 A diagram illustrating an output signal from an A/D converter illustrated in FIG. 3.
Figure 6:
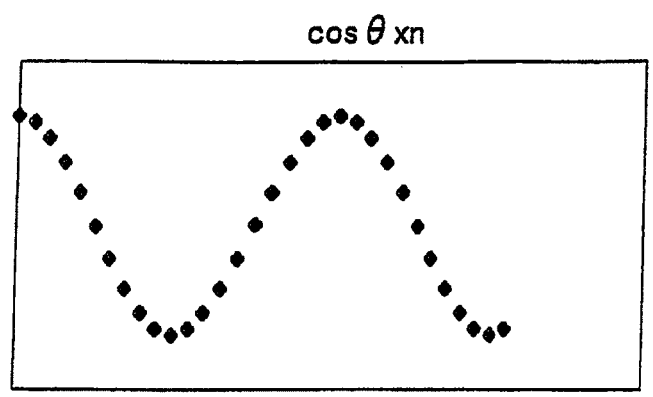
FIG. 6 A diagram illustrating an output signal from a transmitter illustrated in FIG. 3.
Figure 7:
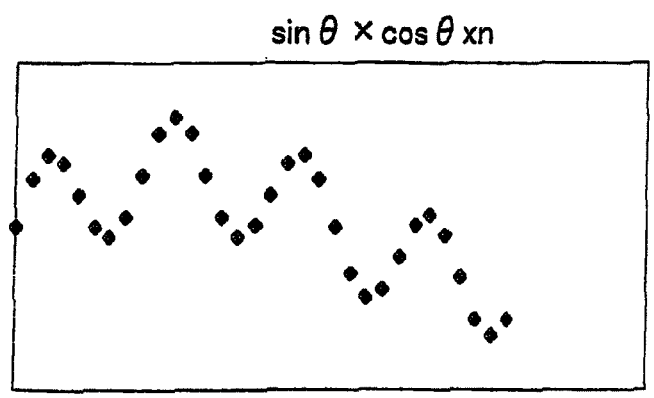
FIG. 7 A diagram illustrating an output signal in a multiplier of a frequency conversion section illustrated in FIG. 3.
Figure 8:
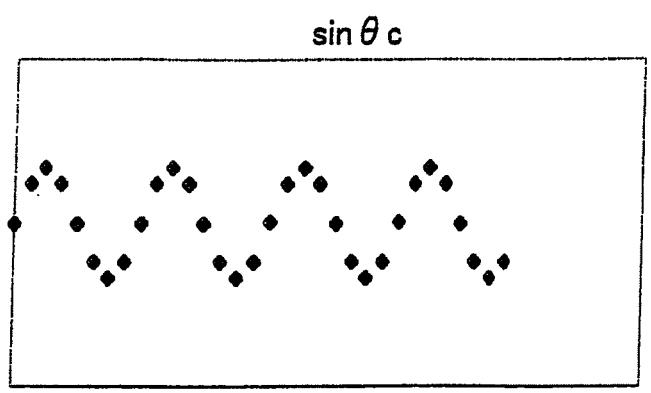
FIG. 8 A diagram illustrating an output signal from the frequency conversion section illustrated in FIG. 3.

FIG. 1 is a principle diagram illustrating a signal processing method and apparatus according to the present invention. FIG. 2 is a detailed circuit diagram for the principle diagram illustrated in FIG. 1. FIG. 3 is a block diagram illustrating a specific structure of the signal processing apparatus illustrated in FIG. 2 using a feedback control method. FIG. 4 illustrates an output signal from an LPF illustrated in FIG. 3. FIG. 5 illustrates an output signal from an A/D converter illustrated in FIG. 3. FIG. 6 illustrates an output signal from a transmitter illustrated in FIG. 3. FIG. 7 illustrates an output signal in a multiplier of a frequency conversion section illustrated in FIG. 3. FIG. 8 illustrates an output signal from the frequency conversion section illustrated in FIG. 3. FIG. 9 are time charts for the specific structure of the signal processing apparatus illustrated in FIG. 3.

Figure 13:
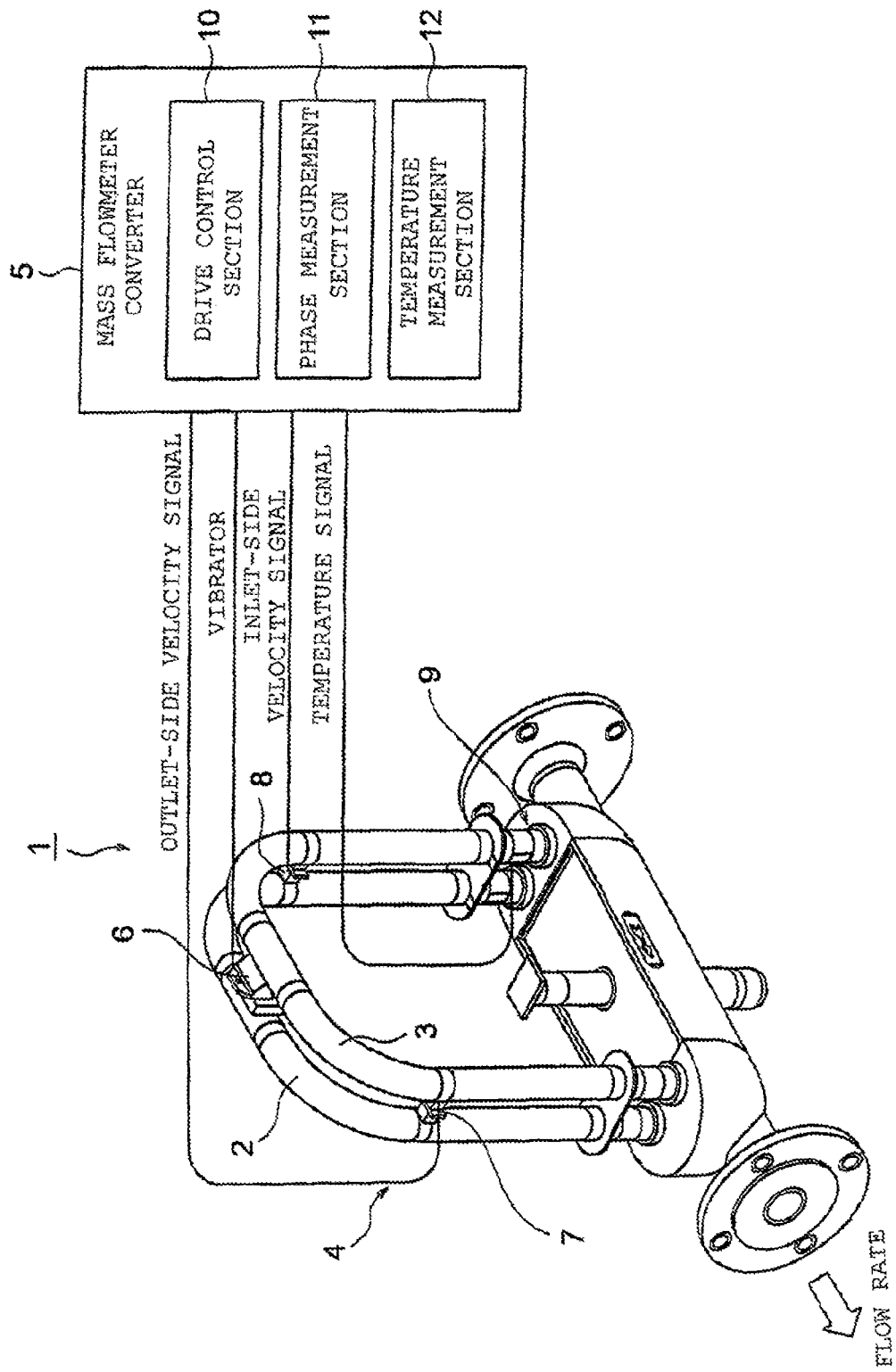
FIG. 13 A structural diagram illustrating a general Coriolis flowmeter to which the present invention is applied.
Figure 14:
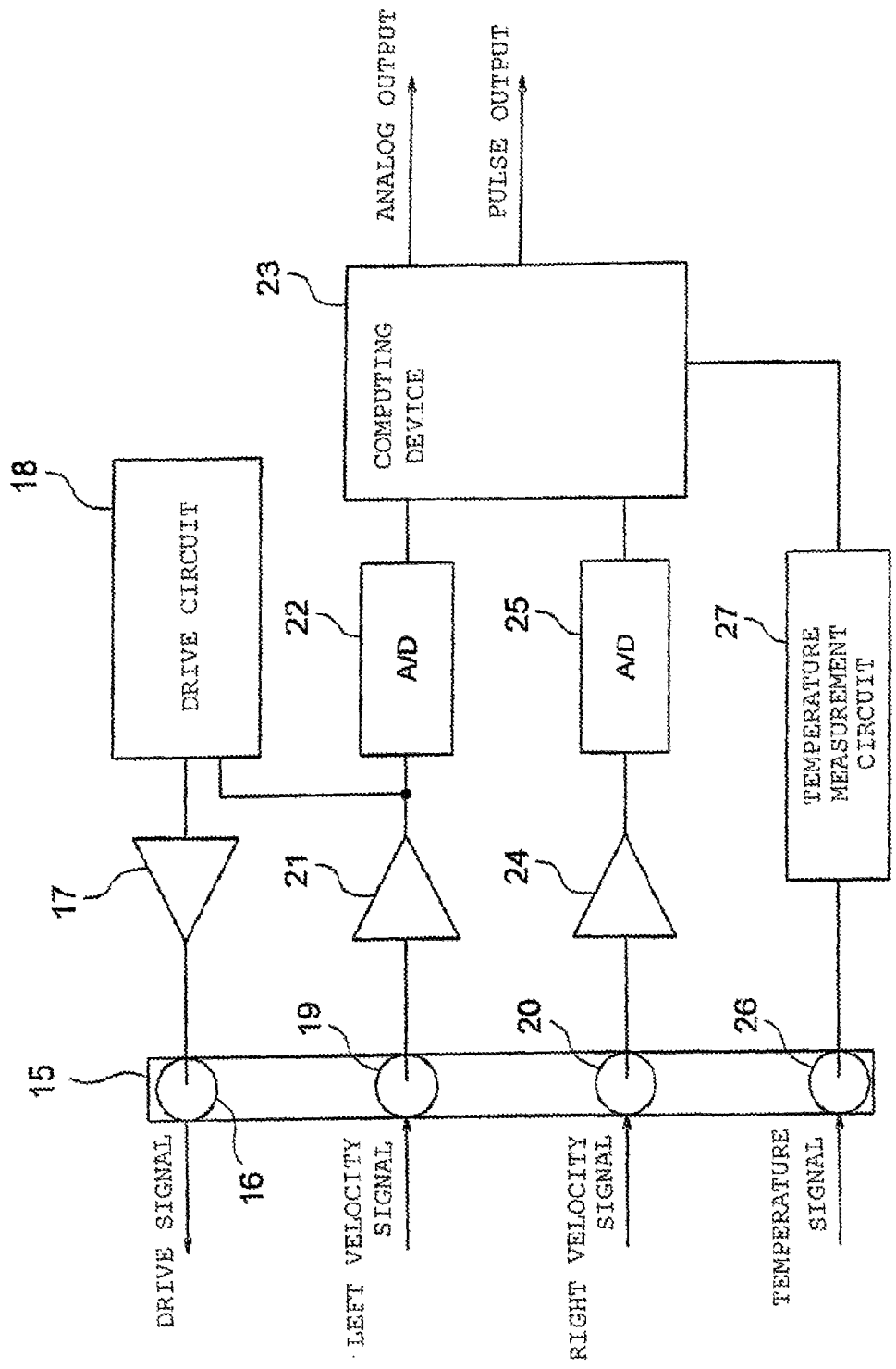
FIG. 14 A block structural diagram illustrating a converter of the Coriolis flowmeter illustrated in FIG. 13.
Figure 15:
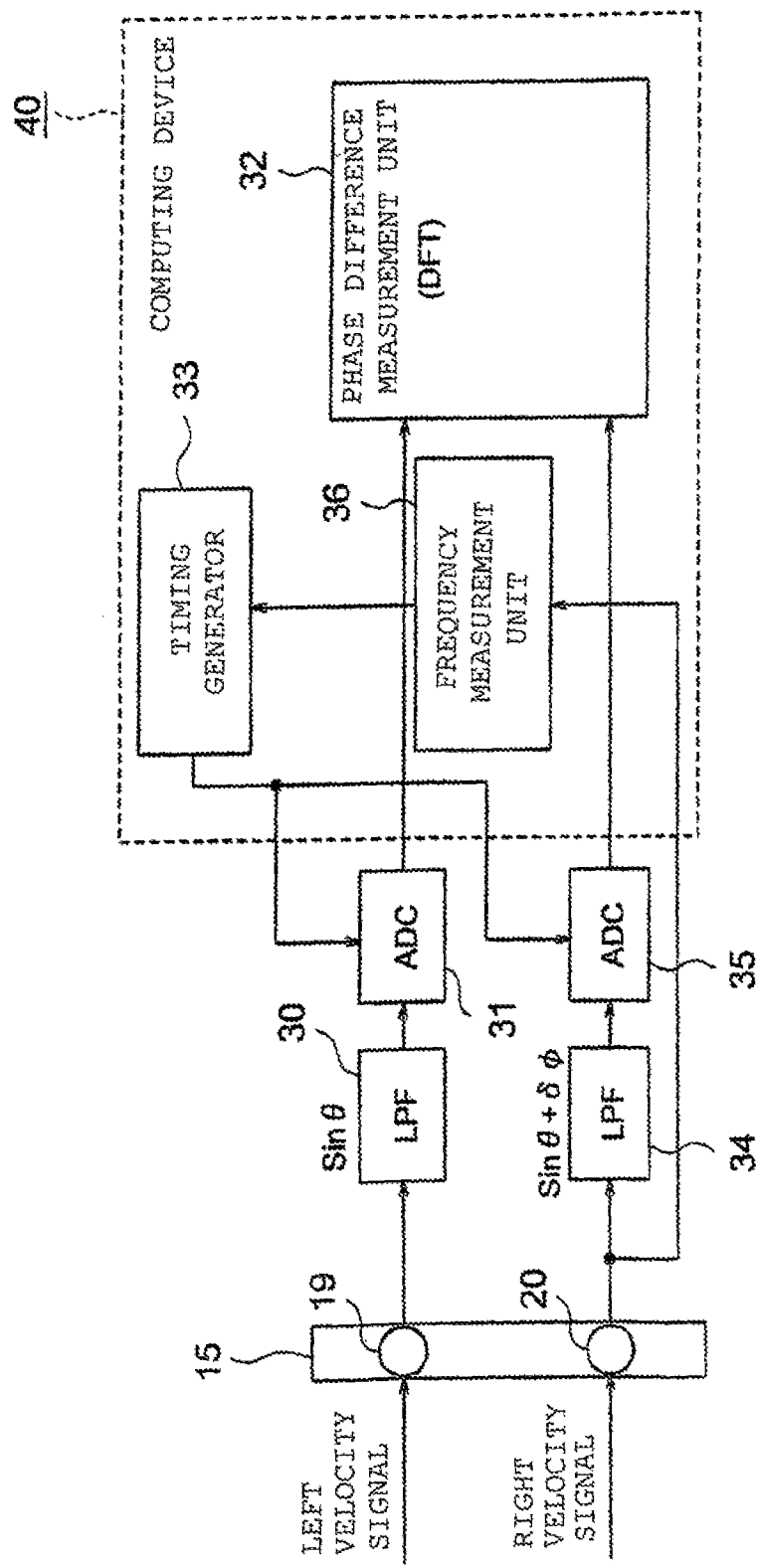
FIG. 15 A block diagram illustrating a phase measurement method using Fourier transform for the converter illustrated in FIG. 14.
Figure 16:
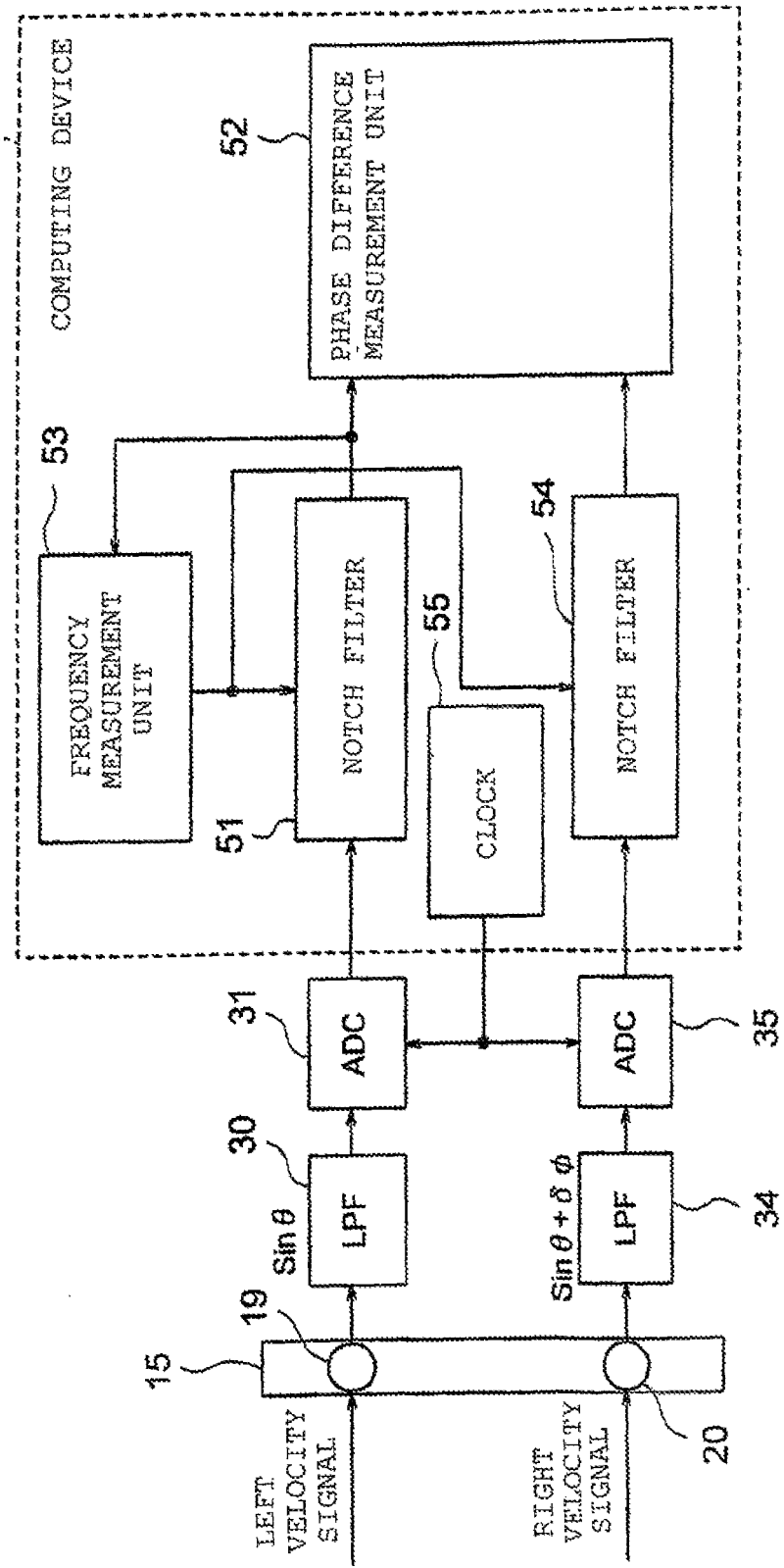
FIG. 16 A block diagram illustrating a phase measurement method using notch filters for the converter illustrated in FIG. 14.
Figure 17:
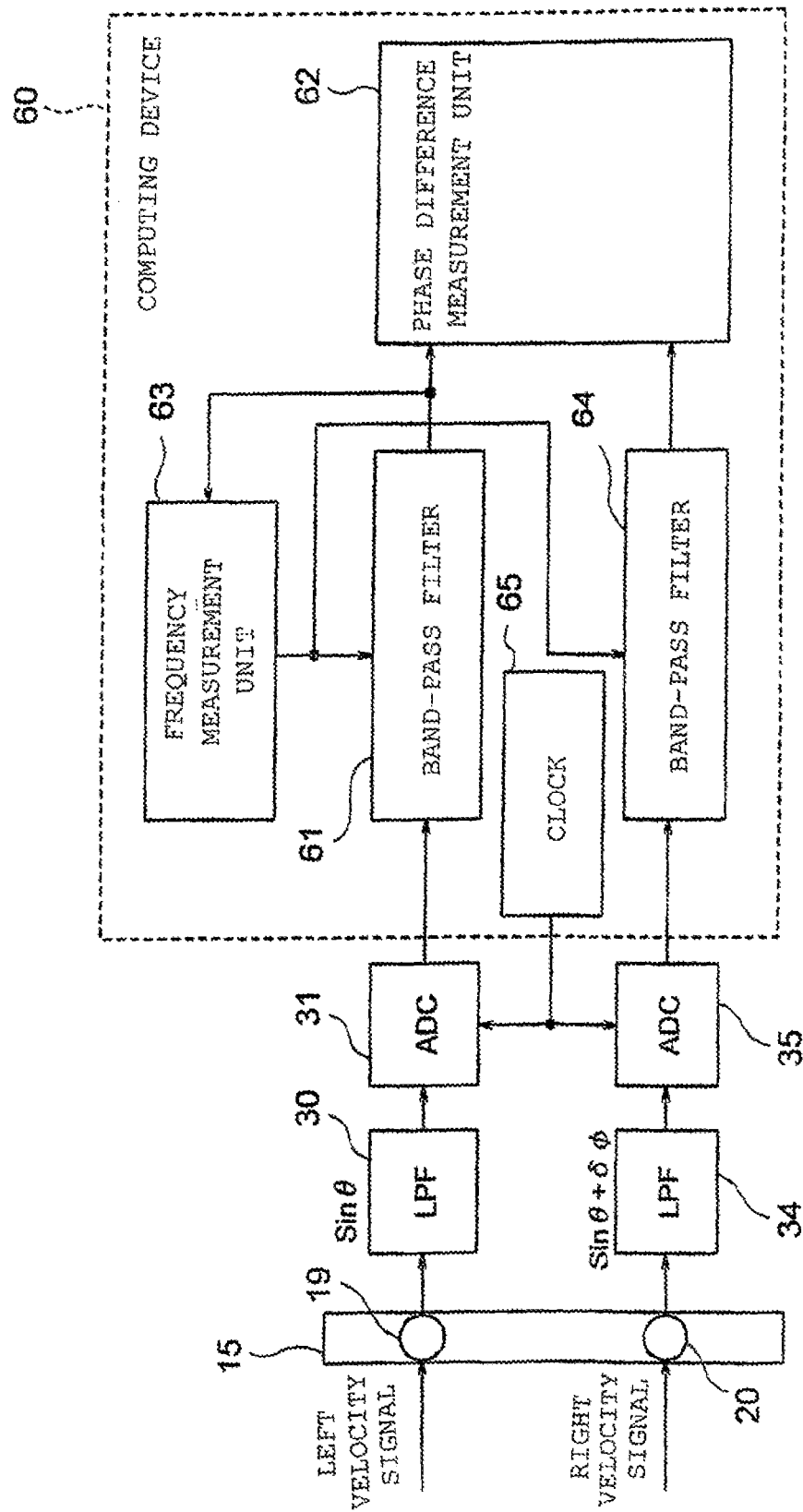
FIG. 17 A block diagram illustrating a phase measurement method using band-pass filters for the converter illustrated in FIG. 14.

In FIG. 1, when measurement tubes 2 and 3 are vibrated by a vibrator (for example, electromagnetic oscillator) 6, vibration velocities generated in the measurement tubes 2 and 3 are detected by a vibration velocity sensor (for example, velocity sensor or acceleration sensor) 70. The detected vibration velocities are computed and processed by a vibration velocity signal computing device 80. The vibration velocity sensor 70 corresponds to the left velocity sensor 7 and the right velocity sensor 8 of FIG. 13.

The vibration velocity signal computing device 80 includes a frequency conversion section 85, a transmitter 90, and a phase difference measurement section 95.

The frequency conversion section 85 performs frequency conversion on the vibration velocities which are generated in the measurement tubes 2 and 3 and detected by the vibration velocity sensor 70 when the measurement tubes 2 and 3 are vibrated by the vibrator 6. A signal from the transmitter 90 is input to the frequency conversion section 85.

Then, signals obtained by frequency conversion by the frequency conversion section 85 are input to the phase difference measurement section 95 provided in a subsequent stage of the frequency conversion section 85. The phase difference measurement section 95 performs A/D conversion on respective velocity signals from the vibration velocity sensor 70, to thereby perform digital conversion processing, and then obtains a phase difference therebetween.

In the signal processing method and apparatus illustrated in FIG. 1, the input signals are subjected to the frequency conversion to control the frequencies after the frequency conversion to constant values, and the phase measurement is performed after the frequency conversion. Therefore, a filter processing apparatus capable of performing high-speed, constant, and high-precision phase measurement even when the frequencies of the input signals change is realized.

That is, in the signal processing method and the apparatus 80 as illustrated in FIG. 1, input frequencies FIN of the input signals from the vibration velocity sensor 70 and an output frequency FX of the transmitter 90 are multiplied by the frequency conversion section 85 to add (or subtract) phase differences of both the signals, and the transmitter 90 is controlled so that the frequencies after the frequency conversion are constant, so as to control the frequencies input to the phase measurement section 95 to a constant value, to thereby perform the phase measurement based on the signals after the frequency conversion.

When such a structure is employed, constant, substantially error-free, and high-speed computation may be realized without providing a large number of filters corresponding to input frequencies and performing any complicated processing such as changing of a computing method.

[Expression 1]

$$Fc = FX + FIN \text{ (or } Fc = FX - FIN) \tag{1}$$

In the computation expression of Expression (1), Fc indicates a frequency after frequency conversion, $F_{IN}$ indicates an input frequency (vibration frequency of measurement flow tube), and $F_X$ indicates a transmission frequency of the transmitter.

A method of obtaining a density of the fluid to be measured is described.

When the density is to be measured, it is necessary to measure vibration frequencies of the measurement tubes 2 and 3. Therefore, frequency values before frequency conversion are desirably obtained.

In the signal processing method and the signal processing apparatus as illustrated in FIG. 1, the vibration velocities which are generated in the measurement tubes 2 and 3 and output from the vibration velocity sensor 7 in the case where the measurement tubes 2 and 3 are vibrated by the vibrator 6 are converted into frequencies by the frequency conversion section 85, and the frequencies obtained by frequency conversion by the frequency conversion section 85 are controlled to constant frequencies.

In the computation expression of Expression (1), the frequency Fc after frequency conversion is always controlled to the constant frequency, and thus is a known value.

Further, $F_X$ indicates the transmission frequency of the transmitter 90. When a value of the transmission frequency $F_X$ of the transmitter 90 is to be controlled to adjust the frequency Fc after frequency conversion to the constant frequency, the transmission frequency $F_X$ of the transmitter 90 is known as a matter of course. When the value of the transmission frequency $F_X$ of the transmitter 90 is not known, the control cannot be performed.

Therefore, substituting the frequency Fc after frequency conversion and the transmission frequency $F_X$ of the transmitter 90, which are known, into Expression (1) may yield the input frequency $F_{IN}$ (vibration frequency of measurement flow tube).

It has been known to express a relationship between a vibration period T of a flow tube and a fluid density ρ as follows in a case where specific constants of a density measurement device (including specific values of used device) are indicated by "A" and "B". In other words, when the specific constants "A" and "B" of the device may be determined, the vibration period T of the flow tube may be measured to obtain the fluid density ρ.

[Expression 2]

$$\rho = AT^2 + B \tag{2}$$

This processing is performed in real time, and hence the density of the fluid to be measured in the measurement tubes 2 and 3 may be obtained.

Note that the detailed density computation expression is described in Japanese Patent Application No. 2001-34989 (JP 2002-243613 A).

FIG. 2 illustrates the specific structure of the signal processing apparatus illustrated in FIG. 1.

In FIG. 2, a left pick-off (LPO) 7 (corresponding to left velocity sensor 7) is connected to a low-pass filter 30. That is, during vibration using the vibrator 6, when a detection signal of a vibration velocity (outlet-side velocity signal) which is generated on the left side of the measurement tubes 2 and 3 is detected by the left pick-off 7, the detection signal of the vibration velocity (outlet-side velocity signal) is input to the low-pass filter 30.

The low-pass filter 30 is a circuit for extracting, through a frequency filter, only a low-frequency left velocity signal (outlet-side velocity signal) from the left velocity signal (outlet-side velocity signal) output from the left velocity sensor 7 detecting the vibration velocity generated on the left side of the measurement tubes 2 and 3 in the case where the measurement tubes 2 and 3 are vibrated by the vibrator 6.

The low-pass filter 30 is connected to an A/D converter 31. The A/D converter 31 converts the left velocity signal (outlet-side velocity signal) which is the analog signal output from the low-pass filter 30 into a digital signal. The left velocity signal (outlet-side velocity signal) obtained as the digital signal by the A/D converter 31 is input to a signal processing apparatus 100.

Further, the signal processing apparatus 100 is connected to the A/D converter 31. The signal processing apparatus 100 frequency-converts the input signal (outlet-side velocity signal) into a desired frequency processed by a phase measurement unit located in a subsequent stage and performs the phase measurement after the frequency conversion, so as to shift the input frequency band and realize stable phase measurement.

On the other hand, a right pick-off (RPO) 8 (corresponding to right velocity sensor 8) is connected to a low-pass filter 34. That is, during vibration using the vibrator 6, when a detection signal of a vibration velocity (inlet-side velocity signal) which is generated on the right side of the measurement tubes 2 and 3 is detected by the right pick-off 8, the detection signal of the vibration velocity (inlet-side velocity signal) is input to the low-pass filter 34.

The low-pass filter 34 is a circuit for extracting, through a frequency filter, only a low-frequency right velocity signal (inlet-side velocity signal) from the right velocity signal (inlet-side velocity signal) output from the right velocity sensor 8 detecting the vibration velocity generated on the right side of the measurement tubes 2 and 3 in the case where the measurement tubes 2 and 3 are vibrated by the vibrator 6.

The low-pass filter 34 is connected to an A/D converter 35. The A/D converter 35 converts the right velocity signal (inlet-side velocity signal) which is the analog signal output from the low-pass filter 34 into a digital signal.

Further, the signal processing apparatus 100 is connected to the A/D converter 35. The signal processing apparatus 100 frequency-converts the input signal (inlet-side velocity signal) into a desired frequency processed by the phase measurement unit located in the subsequent stage and performs the phase measurement after the frequency conversion, so as to shift the input frequency band and realize stable phase measurement.

The A/D converter 31 is connected to a frequency conversion section 110. The frequency conversion section 110 frequency-converts the digital signal of the left velocity signal (outlet-side velocity signal) output from the A/D converter 31 and then input thereto, into the desired frequency processed by the phase measurement unit located in the subsequent stage.

Further, the A/D converter 35 is connected to a frequency conversion section 140. The frequency conversion section 140 frequency-converts the digital signal of the right velocity signal (inlet-side velocity signal) output from the A/D converter 35 and then input thereto, into the desired frequency in the same manner as described above.

Further, a signal from a transmitter 120 is input to the frequency conversion section 110. When the signal output from the transmitter 120 is input to the frequency conversion section 110, the frequency conversion section 110 frequency-converts the input signal (outlet-side velocity signal) input from the left pick-off 7 based on the signal output from the transmitter 120.

A signal obtained by frequency conversion by the frequency conversion section 110 is converted into a desired constant frequency signal based on the output signal from the transmitter 120.

Further, a signal from the transmitter 120 is also input to the frequency conversion section 140. When the signal output from the transmitter 120 is input to the frequency conversion section 140, the frequency conversion section 140 frequency-converts the input signal (inlet-side velocity signal) input from the right pick-off 8 based on the signal output from the transmitter 120.

A signal obtained by frequency conversion by the frequency conversion section 140 is converted into a desired constant frequency signal based on the output signal from the transmitter 120.

When the transmitter 120 is controlled as described above, as in the case of the frequency conversion section 110, also in the frequency conversion section 140, the frequency obtained after performing the frequency conversion, of the right velocity signal (inlet-side velocity signal) input from the A/D converter 35 is controlled to a desired frequency to be processed by a phase measurement unit 130 located in a subsequent stage, based on the output frequency output from the transmitter 120.

The input frequency of the left velocity signal (outlet-side velocity signal) which is output from the A/D converter 31 and input to the frequency conversion section 110 and the input frequency of the right velocity signal (inlet-side velocity signal) which is output from the A/D converter 35 and input to the frequency conversion section 140 are simultaneously subjected to frequency conversion and input to the phase difference measurement unit 130 to perform phase difference measurement.

When such a structure is employed, according to this embodiment, the input frequencies (left velocity signal and right velocity signal) are simultaneously converted into the desired frequency bands. Therefore, even when the input frequencies (left velocity signal and right velocity signal) change, the phase measurement processing frequency is always set to a constant value to significantly reduce the number of filter tables. In addition, the phase measurement processing may be more effectively performed.

According to an effect of the present invention, constant, substantially error-free, and high-speed computation may be realized without providing a large number of filters corresponding to input frequencies and performing any complicated processing such as the change of the computing method. Needless to say, the processing of the phase measurement section may be realized even using a discrete Fourier transform (DFT) or a fast Fourier transform (FFT).

A clock signal is input from a clock 150 to the A/D converter 31 and the A/D converter 35. The clock 150 synchronizes the digital signal of the left velocity signal output from the A/D converter 31 and the digital signal of the right velocity signal output from the A/D converter 35 to realize simultaneous sampling.

The frequency conversion section 110, the transmitter 120, the phase difference measurement unit 130, the frequency conversion section 140, and the clock 150 are included in the signal processing apparatus 100.

The respective input signals (left velocity signal and right velocity signal) which are the digital signals obtained by conversion by the A/D converters 31 and 35 as described above are subjected to the frequency conversion by the frequency conversion sections 110 and 140 based on the output signal from the transmitter 120.

Next, a specific computing method of phase difference measurement computation in the signal processing apparatus 100 illustrated in FIG. 2 is described.

When the measurement tubes 2 and 3 are vibrated by the vibrator 6 of a Coriolis flowmeter 1, the output signals (left velocity signal and right velocity signal) from the vibration detection sensor 70 (left pick-off 7 and right pick-off 8) provided in the measurement tubes 2 and 3 are obtained as input signals of the LPO (left pick-off 7) and the RPO (right pick-off 8) as illustrated in FIG. 2.

In this case, the input signals of the LPO and the RPO are defined as follows (δφ: phase difference between LPO and RPO).

[Expression 3]

Left pick-off: $\sin(\theta)$ (3)

[Expression 4]

Right pick-off: $\sin(\theta+\delta\varphi)$ (4)

The output signals (left velocity signal LPO and right velocity signal RPO) from the two vibration velocity sensors (left pick-off 7 and the right pick-off 8) are converted from the analog signals into the digital signals by the A/D converters 31 and 35 through the low-pass filters 30 and 34 provided in the converter of the Coriolis flowmeter 1, respectively, and then transferred to the signal processing apparatus 100.

As described above, the signal processing apparatus 100 is divided into four blocks including the frequency conversion section 110, the transmitter 120, the phase difference measurement section 130, and the frequency conversion section 140. A phase difference between the output signal LPO from the left pick-off 7 and the output signal RPO from the right pick-off 8 is computed, and then converted into a flow rate signal based on the frequencies output from the vibration velocity sensors and temperature data detected by a temperature sensor 9.

Note that the temperature measurement is not described in the drawing.

The conversion frequency output from the frequency conversion section 110 is obtained by adding (or subtracting) an output frequency θXn output from the transmitter 120 to (or from) an input signal frequency θ output in a case where the left velocity signal (outlet-side velocity signal) which is detected by the left pick-off (left velocity sensor) 7 and extracted as a low-frequency signal by the low-pass filter 30 is converted into the digital signal by the A/D converter 31.

As described above, with respect to the input signal frequency which is output from the frequency conversion section 110 and input to the phase measurement section 130, the input signal frequency θ which is the low-frequency left velocity signal (outlet-side velocity signal) of the digital signal output from the A/D converter 31 is shifted in frequency to another frequency band based on the output frequency θXn output from the transmitter 120 in the frequency conversion section 110.

Therefore, the signal which is shifted in frequency and output by the frequency conversion section 110 and the signal which is shifted in frequency and output by the frequency conversion section 140 having the same processing are subjected to the phase calculation by the phase measurement section 130.

A frequency measurement value (θ+θXn) output from the frequency conversion section 110 is controlled so as to finally become a phase measurement frequency set value θC which is arbitrarily set.

[Expression 5]

$\theta C = \theta + \theta Xn$ (5)

When the transmitter 120 is controlled so that the frequency measurement value (θ+θXn) input to the phase measurement section 130 always becomes the constant frequency θC as described above, high-speed processing of subsequent phase measurement may be achieved.

The frequency control method according to the present invention includes a method for adjusting the frequency of the transmitter 120 so that the output frequencies of the frequency conversion sections (110 and 140) all become equal to θc in the condition of Expression (5), that is, a feedback control method.

Hereinafter, the signal processing method and the signal processing apparatus according to the embodiment of the present invention are described.

FIG. 3 illustrates a specific structure of the signal processing apparatus illustrated in FIG. 2 using the feedback control method.

The signal processing apparatus 100 illustrated in FIG. 3 performs frequency conversion on the input signals (inlet- and outlet-side velocity signals) into desired frequencies and performs phase measurement after the frequency conversion, and hence stable phase measurement may be achieved without taking input frequency bands into account.

In FIG. 3, the A/D converter 31 is connected to the frequency conversion section 110. The frequency conversion section 110 performs frequency conversion on the digital signal of the left velocity signal (outlet-side velocity signal) output and input from the A/D converter 31.

Further, the A/D converter 35 is connected to the frequency conversion section 140. The frequency conversion section 140 performs frequency conversion on the digital signal of the right velocity signal (inlet-side velocity signal) output from the A/D converter 35 and then input thereto.

Further, the frequency conversion section 110 is configured so that the signal from the transmitter 120 is input thereto. When signal output from the transmitter 120 is input to the frequency conversion section 110, the frequency conversion section 110 performs the frequency conversion on the input signal (outlet-side velocity signal) input from the left pick-off 7 based on the signal output from the transmitter 120.

The signal obtained by frequency conversion by the frequency conversion section 110 is converted into the constant frequency signal based on the output signal from the transmitter 120.

Further, the frequency conversion section 140 is also configured so that the signal from the transmitter 120 is input thereto. When signal output from the transmitter 120 is input to the frequency conversion section 140, the frequency conversion section 140 performs the frequency conversion on the input signal (inlet-side velocity signal) input from the right pick-off 8 based on the signal output from the transmitter 120.

The signal obtained by frequency conversion by the frequency conversion section 140 is converted into the constant frequency signal based on the output signal from the transmitter 120.

When the control is made by the modulatable transmitter 120 as described above, as in the case of the frequency conversion section 110, the frequency conversion section 140 also performs the frequency conversion based on the output frequency output from the transmitter 120.

An output end of the frequency conversion section 110 is connected to the frequency measurement section 160 and the phase difference measurement section 130. The frequency measurement section 160 measures the output frequency obtained by frequency conversion by the frequency conversion section 110.

The frequency conversion section 140 is connected to the phase difference measurement unit 130.

The frequency measurement section 160 measures an output signal frequency (θCn=θ+θXn) obtained by adding (or subtracting) the output frequency θXn output from the transmitter 120 to (or from) the input signal frequency θ obtained by converting, into the digital signal, by the A/D converter 31, the low-frequency left velocity signal (outlet-side velocity signal) which is detected by the left pick-off (left velocity sensor) 7 and extracted by the low-pass filter 30, in the frequency conversion section 110.

The frequency measurement value measured by the frequency measurement section 160 is output to the transmitter 120. When the measurement value of the output signal frequency (θCn=θ+θXn) output from the frequency measurement section 160 is input to the transmitter 120, the predetermined frequency signal (θXn) is transmitted based on the measurement value of the output signal frequency (θCn=θ+θXn) and output from the transmitter 120 to the frequency conversion sections 110 and 140.

In the feedback loop which starts at the frequency conversion section 110, passes through the frequency measurement section 160 and the transmitter 120, and returns to the frequency conversion section 110, the output frequency output from the transmitter 120 is added to or subtracted from the input frequency of the left velocity signal (outlet-side velocity signal) input from the A/D converter 31 by the frequency conversion section 110, to perform the frequency conversion in the frequency conversion section 110.

The conversion frequency output from the frequency conversion section 140 is obtained by adding (or subtracting) the output frequency θXn output from the transmitter 120 to (or from) the input signal frequency (θ+δφ) obtained by conversion of the right velocity signal (inlet-side velocity signal) which is detected by the right pick-off (right velocity sensor) 8 and extracted as a low-frequency signal by the low-pass filter 34 into the digital signal by the A/D converter 35.

As described above, with respect to the input signal frequency which is output from the frequency conversion section 140 and input to the phase measurement section 130, the input signal frequency (θ+δφ) which is the low-frequency right velocity signal (inlet-side velocity signal) of the digital signal output from the A/D converter 35 is shifted in frequency to another frequency band based on the output frequency θXn output from the transmitter 120 in the frequency conversion section 140.

When the transmitter 120 is controlled as described above, as in the case of the frequency conversion section 110, also in the frequency conversion section 140, the frequency conversion is performed based on the output frequency θXn output from the transmitter 120.

The modulatable transmitter 120 is controlled in frequency using the very-simple calculation expression as described above.

Further, the frequency conversion section 110 is connected to the phase difference measurement unit 130. Further, the frequency conversion section 140 is connected to the phase difference measurement unit 130.

In the phase difference measurement unit 130, each of the frequency θ of the left velocity signal (outlet-side velocity signal) which is output from the A/D converter 31 and input to the frequency conversion section 110 and the frequency (θ+δφ) of the right velocity signal (inlet-side velocity signal) which is output from the A/D converter 35 and input to the frequency conversion section 140 is converted into the same constant desired frequency, to perform phase difference measurement.

When such a structure is employed, according to this embodiment, the input frequencies (left velocity signal and right velocity signal) are converted into the desired frequency bands. Therefore, the frequency bands of the input frequencies (left velocity signal and right velocity signal) are shifted, and the number of filter tables is significantly reduced. In addition, the phase measurement processing may be more effectively performed.

According to an effect of the present invention, constant, substantially error-free, and high-speed computation may be realized without providing a large number of filters corresponding to input frequencies and performing any complicated processing such as the change of the computing method. Needless to say, the processing of the phase measurement section may be realized even using a discrete Fourier transform (DFT) or a fast Fourier transform (FFT).

The clock signal is input from the clock 150 to the A/D converter 31 and the A/D converter 35. The clock 150 synchronizes the outputs of the A/D converter 31 and the A/D converter 35 and thus has an important function for eliminating a sampling error between the digital signal of the left velocity signal output from the A/D converter 31 and the digital signal of the right velocity signal output from the A/D converter 35.

The respective input signals (left velocity signal and right velocity signal) which are the digital signals obtained by conversion by the A/D converters 31 and 35 as described above are subjected to the frequency conversion by the frequency conversion sections 110 and 140 based on the output signal from the transmitter 120.

Next, a specific phase difference measurement computation in the signal processing apparatus 100 illustrated in FIG. 3 is described.

Hereinafter, phase measurement based on a sum component signal of a modulation composite frequency is described.

The output frequency of the frequency conversion section 110 is measured by the frequency measurement section 160. The transmission frequency of the transmitter 120 is controlled based on the measured value.

In the signal processing apparatus 100, the output frequency of the frequency conversion section 110 is measured by the frequency measurement section 160.

In an initial state, the output signal θXn of the transmitter 120 is not output from the transmitter 120, and hence an initial output signal θX0 from the transmitter 120 is expressed as follows.

[Expression 6]

$$\theta X0 = 0 \quad (6)$$

Therefore, with respect to the flow rate signal LPO which is the output signal (left velocity signal) output from the left pick-off 7 provided for the measurement tubes 2 and 3 in the case where the measurement tubes 2 and 3 are vibrated by the vibrator 6 of the Coriolis flowmeter 1, a sum component frequency of a frequency to be frequency modulated may be expressed by "(θ+θXn)". In a case of θXn=θX0, the output signal frequency of the frequency converter 110 is expressed as follows based on Expression (6).

[Expression 7]

$$\theta co = \theta + \theta X0 = \theta \quad (7)$$

Thus, an initial measurement frequency is activated based on the LPO signal frequency θ.

An output signal θX1 from the transmitter 120 in a next first step is compared with the initial measurement frequency such that (phase measurement frequency θC)=(target frequency set value)=const. As expressed by the following Expression (8), θX1 is determined such that the difference becomes the output signal of the transmitter 120.

The transmitter frequency θX1 is obtained as follows.

[Expression 8]

$$\theta X1 = \theta C - \theta \quad (8)$$

When the transmitter frequency θX1 in the first step is obtained, θC=const.

An output signal frequency of the frequency conversion section 110 which is to be set for an output signal θX2 from the transmitter 120 in a next step is expressed as follows.

[Expression 9]

$$\theta+\theta X1 = \theta C1 \quad (9)$$

Therefore, the output signal θX2 from the transmitter 120 in the next step is expressed as follows based on Expression (8).

[Expression 10]

$$\theta X2 = \theta X1 + \theta C - (\theta + \theta X1) \quad (10)$$

When the operation described above is repeated, the following is obtained.

[Expression 11]

$$\theta_{X3} = \theta_{X2} + \theta_c - (\theta + \theta_{X2})$$
$$\theta_{X4} = \theta_{X3} + \theta_c - (\theta + \theta_{X3})$$
$$\vdots$$
$$\theta_{Xn} = \theta_{Xn-1} + \theta_c - (\theta + \theta_{Xn-1})$$
(11)

When the output frequency θXn from the transmitter 120 is controlled based on a real-time processing clock of the clock 150 as described above, θXn≈θXn−1.

Therefore, the output signal frequency (θ+θXn) of the frequency conversion section 110 is finally expressed as follows.

[Expression 12]

$$\theta C = \theta + \theta Xn \quad (12)$$

Thus, high-speed processing of subsequent phase measurement may be achieved using Expression (12) in time series processing.

In the low-pass filter 30 illustrated in FIG. 3, when a harmonic noise is removed to eliminate the influence of aliasing in A/D conversion, a sine signal (sin θ) as illustrated in FIG. 4 is output.

The sine signal (sin θ) output from the low-pass filter 30 as illustrated in FIG. 4 is sampled for digital signal conversion at an arbitrary constant interval by the A/D converter 31 to obtain a sampling signal (sin θ) as illustrated in FIG. 5, and then output from the A/D converter 31.

The signal (sin θ) as illustrated in FIG. 5, which is output from the low-pass filter 30 and sampled for digital signal conversion by the A/D converter 31, is input to the frequency conversion section 110 of the signal processing apparatus 100 illustrated in FIG. 3. Further, a transmitter output signal output from the transmitter 120 is input to the frequency conversion section 110.

When the measurement value of the output signal frequency (θCn=θ+θXn) output from the frequency measurement section 160 is input to the transmitter 120, the transmission frequency signal (θXn) of the transmitter 120 is transmitted at a desired frequency based on the measurement value of the output signal frequency (θCn=θ+θXn), and a cosine signal (cos θXn) as illustrated in FIG. 6 is output at the same transmission output rate as the sampling interval of the input signal in the A/D converter 31.

When the output signal (cos θXn) from the transmitter 120 is input to the frequency conversion section 110, in the frequency conversion section 110, the signal (sin θ) as illustrated in FIG. 5, which is sampled for digital signal conversion by the A/D converter 31, is multiplied by the output signal (cos θXn) output from the transmitter 120 as illustrated in FIG. 6 (sin θ×cos θXn) by a multiplier provided in the frequency conversion section 110, to thereby obtain a signal (sin θ×cos θXn) as illustrated in FIG. 7.

The signal (sin θ×cos θXn) as illustrated in FIG. 7, which is obtained by multiplication (sin θ×cos θXn) by the multiplier provided in the frequency conversion section 110, passes through a high-pass filter (HPF) provided in the frequency conversion section 110 to remove a low-frequency component, to thereby obtain a signal (sin θC) as illustrated in FIG. 8. The signal (sin θC) as illustrated in FIG. 8 is output from the frequency conversion section 110 and input to the frequency measurement section 160 and the phase difference measurement unit 130.

The phase difference between the output signals (left velocity signal and right velocity signal) from the vibration velocity sensor 70 (left pick-off 7 and right pick-off 8) provided in the measurement tubes 2 and 3 in the case where the measurement tubes 2 and 3 are vibrated by the vibrator 6 of the Coriolis flowmeter 1 is computed by the four blocks including the frequency conversion sections 110 and 140, the transmitter 120, the phase difference measurement unit 130, and the frequency measurement section 160, included in the signal processing apparatus 100 illustrated in FIG. 3. Then, the computed phase difference is converted into the flow rate signal based on the frequency signal output from the frequency measurement section 160 and the temperature data detected by the temperature sensor 9.

Next, an operation of the signal processing apparatus 100 illustrated in FIG. 3 is described with reference to time charts illustrated in FIG. 9.

First, in the low-pass filter 30 illustrated in FIG. 3, when a harmonic noise is removed to eliminate the influence of aliasing in A/D conversion, a sine signal (sin θ) as illustrated in FIG. 5 is output.

When the sine signal (sin θ) illustrated in FIG. 5 is output, the sine signal (sin θ) illustrated in FIG. 5 is input to the A/D converter 31. Then, the signal is sampled for digital signal conversion at an arbitrary constant interval by the A/D converter 31 to obtain a sampling signal (Y1=sin θ) as illustrated in FIG. 9(A) and output from the A/D converter 31.

The sampling signal (sin θ) illustrated in FIG. 9(A), which is output from the A/D converter 31, is input to the frequency conversion section 110 of the signal processing apparatus 100 illustrated in FIG. 3.

On the other hand, the frequency (θCn=θ+θXn) signal measured based on the signal output from the frequency conversion section 110 is output from the frequency measurement section 160 of the signal processing apparatus 100. In the transmitter 120 to which the measurement value of the output signal frequency (θCn=θ+θXn) output from the frequency measurement section 160 is input, the desired transmission frequency signal (θXn) is transmitted based on the measurement value of the output signal frequency (θCn=θ+ θXn), and a cosine signal (Y2=cos θXn) as illustrated in FIG. 9(B) is output at the same transmission output rate as the sampling interval of the input signal in the A/D converter 31.

When the cosine signal (Y2=cos θXn) illustrated in FIG. 9(B) is input to the frequency conversion section 110 from the transmitter 120, the cosine signal is multiplied by the sampling signal (Y1=sin θ) illustrated in FIG. 9(A), which is output from the A/D converter 31, (sin θ×cos θXn) by the multiplier provided in the frequency conversion section 110 to obtain a signal (Y3=sin θ×cos θXn) as illustrated in FIG. 9(C).

The signal (Y3=sin θ×cos θXn) as illustrated in FIG. 9(C), which is obtained by multiplication (sin θ×cos θXn) by the multiplier provided in the frequency conversion section 110, passes through a high-pass filter (HPF) provided in the frequency conversion section 110 to remove a low-frequency component, to thereby obtain a signal (Y4=½·sin θC) as illustrated in FIG. 9(D). The signal (Y4=½·sin θC) as illustrated in FIG. 9(D) is output from the frequency conversion section 110 and input to the frequency measurement section 160 and the phase difference measurement unit 130.

Further, in the low-pass filter 34 illustrated in FIG. 3, when a harmonic noise is removed to eliminate the influence of aliasing in A/D conversion, a sine signal (sin(θ+δϕ)) is output.

When the sine signal (sin(θ+δϕ)) is output, the sine signal (sin(θ+δϕ)) is input to the A/D converter 35. Then, the signal is sampled for digital signal conversion at an arbitrary constant interval by the A/D converter 35.

The signal output from the A/D converter 35 is multiplied by the sampling signal output from the A/D converter 35 by a multiplier provided in the frequency conversion section 140 to obtain a signal.

The signal obtained by multiplication by the multiplier provided in the frequency conversion section 140 passes through a high-pass filter (HPF) provided in the frequency conversion section 110 to remove a low-frequency component, to thereby obtain a signal (Y5=½·sin(θC+δϕ)) as illustrated in FIG. 9(E). The signal (Y5=½·sin(θC+δϕ)) illustrated in FIG. 9(E) is output from the frequency conversion section 110 and input to the phase difference measurement unit 130.

In the phase difference measurement unit 130, a signal (Y6=δϕ) illustrated in FIG. 9(F) is output as a phase difference δϕ based on the signal (Y4=½·sin θC) illustrated in FIG. 9(D), which is output from the frequency conversion section 110 and input to the phase difference measurement unit 130, and the signal (Y5=½·sin(θC+δϕ)) illustrated in FIG. 9(E), which is output from the frequency conversion section 140 and input to the phase difference measurement unit 130.

When the computing interval is synchronized with the sampling time as described above, the real time performance for phase measurement may be improved.

Further, each of the set of vibration velocity signals (sin θ and sin(θ+δϕ)) is subjected to the same processing for phase calculation, and hence there is almost no computing error. Therefore, accurate phase calculation may be achieved.

Embodiment 2

Next, the signal processing method is described with reference to the operational flow chart illustrated in FIG. 10.

Figure 10:
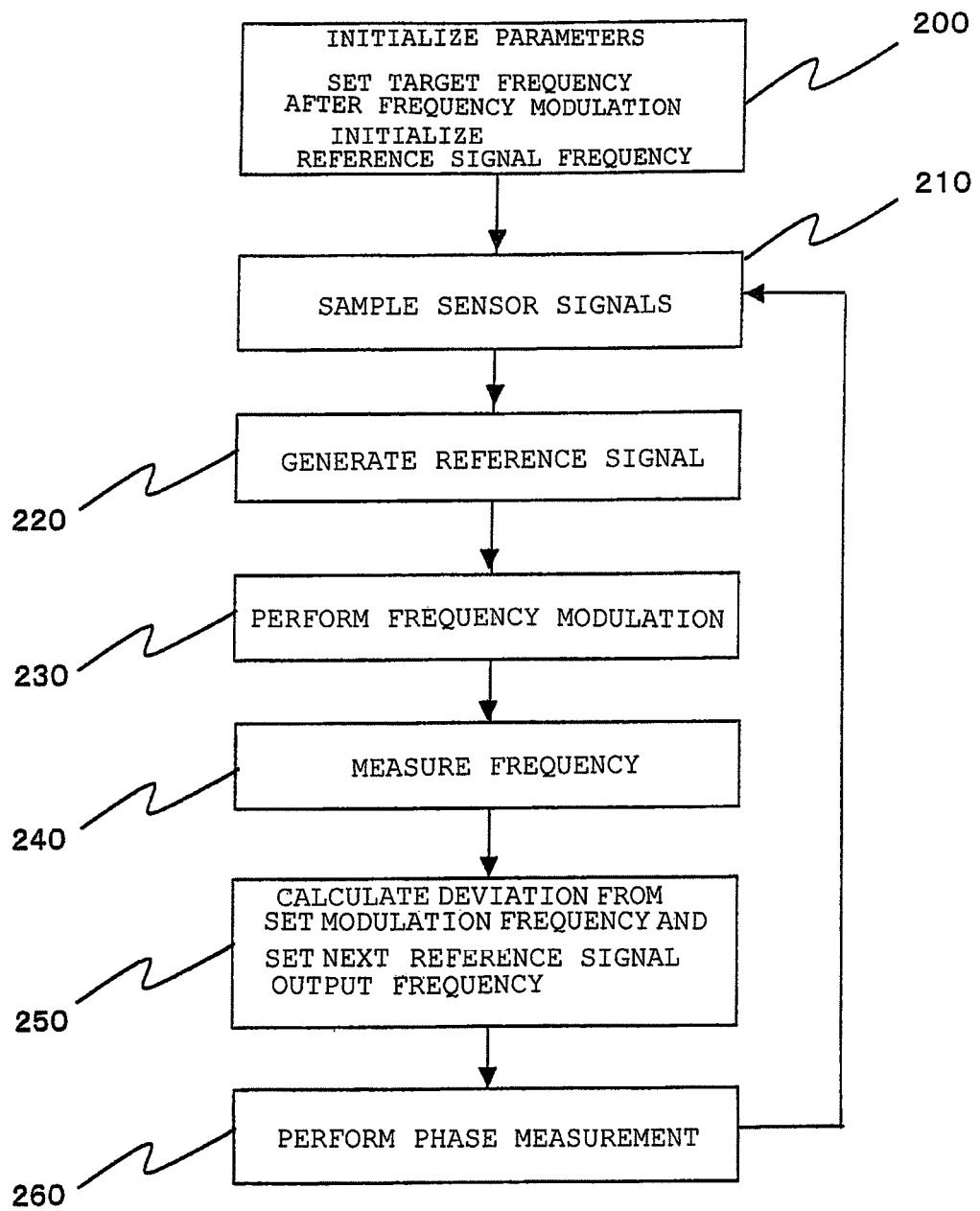
FIG. 10 An operational flowchart for the specific structure of the signal processing apparatus illustrated in FIG. 3.

FIG. 10 is a flow chart illustrating frequency modulation and phase measurement in a case where the feedback loop is used.

In FIG. 10, in Step 200, parameters of the signal processing apparatus 100 which is the computing device are initialized. When the parameters of the signal processing apparatus 100 are initialized, in Step 200, a target frequency for frequency modulation, that is, a target frequency after frequency modulation is set, and further, a frequency of an initial reference waveform is set, that is, a reference signal frequency is initially set.

When the parameters of the signal processing apparatus 100 which is the computing device are initialized, the target frequency after frequency modulation is set, and the reference signal frequency is initially set in Step 200, in Step 210, a phase and velocity signal output from the left pick-off (LPO) 7 (left velocity sensor 7) is sampled for digital signal conversion at an arbitrary sampling interval by the A/D converter 31, and a phase and velocity signal output from the right pick-off (RPO) 8 (right velocity sensor 8) is sampled for digital signal conversion at an arbitrary sampling interval by the A/D converter 35.

The phase and velocity signal sampled for digital signal conversion at the arbitrary sampling interval by the A/D converter 31 is input to the frequency converter 110. The phase and velocity signal sampled for digital signal conversion at the arbitrary sampling interval by the A/D converter 35 is input to the frequency converter 140.

When the phase and velocity signal is sampled for digital signal conversion at an arbitrary sampling interval in Step 210, in Step 220, the output frequency is set for the transmitter 120 for reference signal, to thereby generate the reference signal. When the reference signal is generated, the reference signal having the frequency set in the transmitter 120 is output from the transmitter 120 and input to the frequency converters 110 and 140.

When the reference signal is generated in the transmitter 120 in Step 220, the processing of the frequency converters 110 and 140 is performed in Step 230. Therefore, the frequency converter 110 to which the reference frequency signal output from the transmitter 120 is input converts the phase and velocity signal output from the A/D converter 31 into a phase and velocity signal having an arbitrary frequency based on the reference signal output from the transmitter 120.

Further, the frequency converter 140 to which the reference frequency signal output from the transmitter 120 is input converts the phase and velocity signal output from the A/D converter 35 into a phase and velocity signal having an arbitrary frequency based on the reference signal output from the transmitter 120.

When the conversion into the phase and velocity signal of the arbitrary frequency is performed in Step 230, the frequency after frequency conversion is measured in Step 240 and compared with the target frequency for frequency modulation at the initial setting.

That is, the phase and velocity signal which is output from the A/D converter 31 and obtained by the arbitrary frequency conversion by the frequency converter 110 is input to the frequency measurement unit 160 and the phase measurement unit 130. Then, the frequency after frequency conversion is measured by the frequency measurement unit 160 and compared with the target frequency for frequency modulation at the initial setting, which is output from the transmitter 120.

When the comparison with the target frequency for frequency modulation at the initial setting is made in Step 240, a next reference signal transmission frequency output from the transmitter 120 is determined in Step 250.

That is, in Step 250, the next reference signal transmission frequency output from the transmitter 120 is determined such that a difference frequency obtained by the comparison in Step 240 becomes 0 Hz.

When the next reference signal transmission frequency output from the transmitter 120 is determined in Step 250, the phase measurement is performed in Step 260.

That is, in Step 260, the phase and velocity signal obtained by the arbitrary constant frequency conversion based on the transmission frequency of the reference signal output from the transmitter 120 is input to the phase measurement unit 130. The phase measurement unit 130 performs the phase measurement using a FFT or the like based on the phase and velocity signal obtained by the arbitrary constant frequency conversion, which is output from the frequency converter 110. When the phase measurement is performed using the FFT or the like as described above, high-precision phase difference measurement may be always performed at the same computing interval.

Hereinafter, the four blocks including the frequency conversion sections 110 and 140, the transmitter 120, the phase difference measurement unit 130, and the frequency measurement section 160, included in the signal processing apparatus 100 are described.

(1) Frequency Conversion Section

Figure 11:
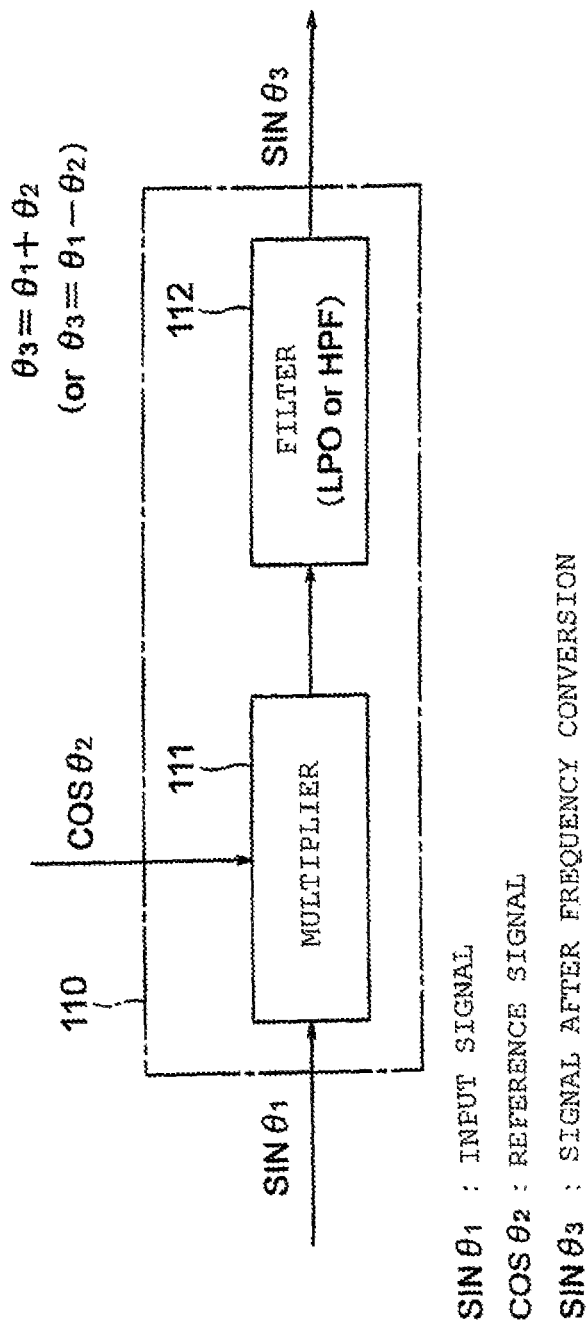
FIG. 11 A block structural diagram illustrating the frequency conversion section of the signal processing apparatus illustrated in FIG. 3.

The frequency conversion section 110 of the signal processing apparatus 100 has a structure as illustrated in FIG. 11.

In FIG. 11, the frequency conversion section 110 includes a multiplier 111, a low-pass filter (LPF) 112 (or high-pass filter (HPF)).

A reference signal cos θ2 from the transmitter 120 and an input signal SIN θ1 from the A/D converter 31 are multiplied by each other and then subjected to filter processing by the low-pass filter 112.

The reference signal cos θ2 from the transmitter 120 is multiplied by an input signal sin θ1 obtained by converting, into a digital signal, by the A/D converter 31, the low-frequency left velocity signal (outlet-side velocity signal) which is detected by the left pick-off (left velocity sensor) 7 and extracted by the low-pass filter 30 and then output therefrom, to thereby combine sum and difference frequency signals.

[Expression 13]

$$\sin\theta1 \cdot \cos\theta2 = \frac{1}{2}(\sin(\theta1+\theta2)+\sin(\theta1-\theta2)) \quad (13)$$

The sum and difference frequency signals are filtered by the low-pass filter (or high-pass filter) 112 to extract only the difference signal (or sum signal).

In this case, for specific description, the sum signal is extracted. However, even when the difference signal is extracted, there is no problem, and hence the filter processing method is applied as appropriate according to the frequency conversion method.

The output from the low-pass filter (or high-pass filter) 112 is expressed as follows.

[Expression 14]

$$\frac{1}{2}(\sin(\theta1+\theta2)) \quad (14)$$

In this case, an output signal frequency θ3 from the low-pass filter (or high-pass filter) 112 is always controlled to a constant value.

Therefore, the same filter may be always used without depending on the input signal.

Thus, the phase measurement in the phase difference measurement unit 130 located in the subsequent stage of the frequency conversion section 110 may be highly uniformed and simplified.

(2) Frequency Measurement Section

In this embodiment, the principle of phase-locked loop (PLL) is used for the frequency measurement method. The PLL is a known electronic circuit in which a signal which is equal in frequency to an input alternating current signal and locked in phase therewith is output from another oscillator by feedback control.

Therefore, the PLL is fundamentally a phase-lock circuit and may produce a signal locked in phase with an input signal.

The PLL is an oscillation circuit for feedback-controlling an oscillator in a loop for oscillation so that a phase difference between a reference signal input from an outside and an output from the oscillator in the loop is constant. Therefore, the PLL may be relatively easily constructed using a computing device and may perform high-speed computation.

Figure 12:
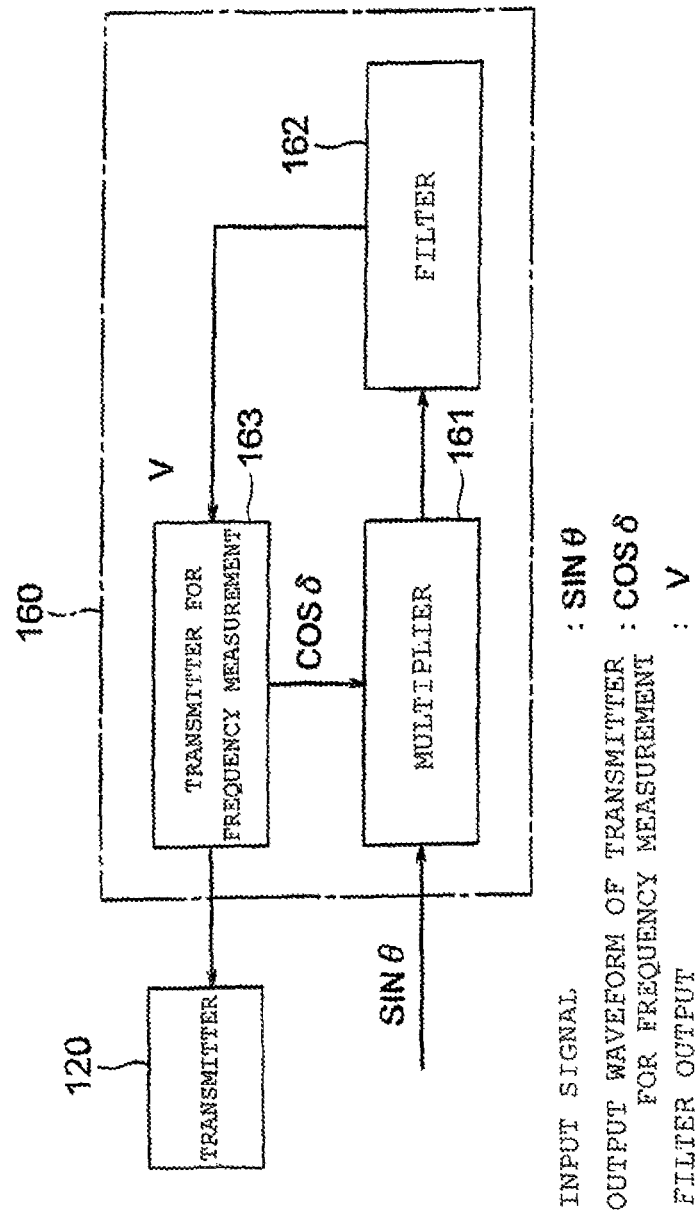
FIG. 12 A block structural diagram illustrating a frequency measurement section of the signal processing apparatus illustrated in FIG. 3.

The frequency measurement section 160 of the signal processing apparatus 100 has a structure as illustrated in FIG. 12.

In FIG. 12, the frequency measurement section 160 includes a multiplier 161, a low-pass filter (LPF) 162, and a transmitter 163 for frequency measurement.

The frequency conversion section 110 is connected to the multiplier 161. A conversion frequency signal sin(θ+θXn) obtained by adding (or subtracting) the output frequency θXn output from the transmitter 120 to (or from) the input signal frequency θ obtained by converting, into the digital signal, by the A/D converter 31, the low-frequency left velocity signal (outlet-side velocity signal) which is detected by the left pick-off (left velocity sensor) 7 and extracted by the low-pass filter 30, is output from the frequency conversion section 110 and input to the multiplier 161.

Then, the multiplier 161 compares the phase of an output signal of the frequency conversion section 110 with the phase of an output signal cos δ output from the transmitter 163 for frequency measurement and outputs the signals as a difference signal and a sum signal to the low-pass filter 162.

Therefore, an output end of the multiplier 161 is connected to the low-pass filter 162. The low-pass filter 162 extracts only a low-frequency signal from the output signal output from the multiplier 161 through a frequency filter.

Thus, in this case, only a difference component is extracted from the output signal output from the multiplier 161.

The low-pass filter 162 is connected to the transmitter 163 for frequency measurement. The transmitter 163 for frequency measurement generates phase data 6 based on the low-frequency signal output from the low-pass filter 162.

A feedback loop is formed so that output data "V" (frequency computing function V) of only the difference component obtained by filtering by the low-pass filter 162 becomes 0.

As illustrated in FIG. 12, the input signal which is output from the frequency conversion section 110 and input to the multiplier 161 is expressed by SIN θ and the output signal which is output from the transmitter 120 and input to the multiplier 161 is expressed by cos δ. When the two waveforms are multiplied by the multiplier 161, the following is obtained.

[Expression 15]

$$\sin\theta \cdot \cos\delta = \frac{1}{2}(\sin(\theta+\delta)+\sin(\theta-\delta)) \quad (15)$$

Input waveform: sin θ

Output waveform of transmitter for frequency measurement: cos δ

When a result obtained by multiplication by the multiplier 161 as expressed by Expression (14) is filtered by the low-pass filter 162, a high-frequency component is removed to obtain the following expression.

[Expression 16]

$$V=\sin(\theta-\delta) \quad (16)$$

When a value of (θ−δ) in Expression (15) is a sufficiently small value (V≈0), the frequency computing function V indicating the result obtained by multiplication by the multiplier 161 may be approximately expressed as follows.

[Expression 17]

$$V = \theta - \delta \approx 0 \quad (17)$$

When an output waveform of the transmitter 163 for frequency measurement is controlled so that the frequency computing function V becomes 0, the preceding phase θ obtained by frequency conversion by the frequency conversion section 110 may be obtained.

When the phase θ output from the frequency conversion section 110, which is obtained after the frequency conversion as described above is computed using the following Expressions (18) and (19), a frequency "f" may be obtained.

[Expression 18]

$$\frac{\Delta \theta}{\Delta T} = \omega = 2 \cdot \pi \cdot f \quad (18)$$

ω: Angular velocity (rad/s)

Note that ΔT indicates a change in time and is equal to the computing interval (sampling rate).

Therefore, a change in phase (θ) is as follows.

[Expression 19]

$$\theta = 2 \cdot \pi \cdot f \cdot Ta \quad (19)$$

where

Ta: change in time (sampling interval) (sec.)
f: input frequency (Hz)
θ: change in phase (rad)
The input frequency "f" is as follows.

[Expression 20]

$$f = \frac{\theta}{2 \cdot \pi \cdot T} \quad (20)$$

T: sampling interval

When such calculation is performed by the frequency measurement unit 160, high-speed frequency measurement may be achieved.

(3) Transmitter

In FIG. 3, the output frequency of the modulatable transmitter 120 is controlled based on the result (θ+θXn) obtained by measurement by the frequency measurement section 160.

That is, in the transmitter 120, the frequency θ of the detection signal of the vibration velocity (outlet-side velocity signal) generated on the left side of the measurement tubes 2 and 3, which is detected by the left pick-off 7 and input to the frequency conversion section 110 in the case where the measurement tubes 2 and 3 are vibrated by the vibrator 6, is controlled to a desired frequency to be processed by the phase difference measurement unit 130.

The frequency conversion section 110 and the frequency conversion section 140 have the same structure. Therefore, as in the case of the frequency output from the frequency conversion section 110, the frequency output from the frequency conversion section 140, more specifically, the frequency (θ+δφ) of the detection signal of the vibration velocity (inlet-side velocity signal) generated on the right side of the measurement tubes 2 and 3, which is detected by the right pick-off 8 and input to the frequency conversion section 140 in the case where the measurement tubes 2 and 3 are vibrated by the vibrator 6, is converted into a desired frequency.

(4) Phase Difference Measurement Unit

There are various phase measurement methods. In a case of phase measurement using a Fourier transform, a frequency is fixed, and hence very-high-speed computation may be achieved.

Hereinafter, an example of a discrete Fourier transform (DFT) is described. The discrete Fourier transform is a Fourier transform on a discrete group, often used for frequency analysis of discrete digital signals in signal processing, and also used to efficiently calculate a partial differential equation or a convolution integral. The discrete Fourier transform may be calculated with high speed (by a computer) using a fast-Fourier transform (FFT).

When the input signal sampled in the phase difference measurement unit 130 is expressed by g(n), DFT-G(k) is defined as follows.

[Expression 21]

$$G(k) = \sum_{n=0}^{N-1} g(n) \exp\left(\frac{-j \cdot 2 \cdot \pi \cdot n \cdot k}{N}\right) \quad (21)$$

$$= \sum_{n=0}^{N-1} g(n)\left(\cos\left(\frac{2 \cdot \pi \cdot n \cdot k}{N}\right) - j\sin\left(\frac{2 \cdot \pi \cdot n \cdot k}{N}\right)\right)$$

$$k = 0, 1, \ldots, N-1$$

For simpler expression, when a complex exponential function part is expressed by the following substitution,

[Expression 22]

$$W_N = \exp\left(\frac{-j \cdot 2\pi}{N}\right) \quad (22)$$

$$= \cos\left(\frac{2\pi}{N}\right) - j\sin\left(\frac{2\pi}{N}\right)$$

Expression (21) is expressed as follows.

[Expression 23]

$$G(k) = \sum_{n=0}^{N-1} g(n) \cdot W_N^{nk} \quad (23)$$

Assume that attention is focused on a complex exponential function WNnk, and N is expressed by N=2M (M: integer), and, for example, N=8. When the input frequency is ¼ of the sampling frequency, a real part function and an imaginary part function may be expressed as follows by 0.1, and −1 because of the periodicity of trigonometric functions.

[Expression 24]

| Real | Imaginary | (24) |
|---|---|---|
| $W_8^0$ | 1 | 0 |
| $W_8^2$ | 0 | −1 |
| $W_8^4$ | −1 | 0 |
| $W_8^6$ | 0 | 1 |

Therefore, the input signals LPO and RPO obtained by frequency conversion into ¼ of the sampling frequency may be very simply subjected to the Fourier transform. In normal phase measurement, only a single frequency (vibration frequency) is desirably subjected to the Fourier transform and conversion for another frequency band is not performed, and hence computation may be performed by only addition and subtraction.

In fact, when the input signal input to the phase difference measurement section 130 is expressed by g(n), the input signal g(n) is a frequency of ¼ of the sampling rate, and N is expressed by N=2M (M: integer), DFT-G(n) may be computed as follows.

[Expression 25]

$$
\begin{array}{cc}
\text{Calculation of} & \text{Calculation of} \\
\text{real part (Re)} & \text{imaginary part (Re)} \\
g_n \times 1 & g_n \times 0 \\
g_{n+1} \times 0 & g_{n+1} \times -1 \\
g_{n+2} \times -1 & g_{n+2} \times 0 \\
\vdots & \vdots \\
\cdots & \cdots \\
\vdots & \vdots \\
g_{n+N-2} \times -1 & g_{n+N-2} \times 0 \\
+) \quad g_{n+N-1} \times 0 & g_{n+N-1} \times 1 \\
\hline
\text{Re} = g_n - g_{n+2} \cdots - g_{n+N-2} & \text{Im} = -g_{n+1} \cdots + g_{n+N-1}
\end{array}
\tag{25}
$$

Even when the value of M increases, fundamental computation does not completely change. Therefore, when M increases, calculation may be performed with very high precision and a computing load almost does not change.

When two input signals are subjected to the discrete Fourier transform (DFT) in the procedure described above, the RPO signal may be substituted as follows,

[Expression 26]

$$\text{RPO signal:} \quad \frac{1}{2}(\sin(\theta + \theta_x)) = \frac{1}{2}(\sin(\theta_c))\frac{1}{2}\exp(j\theta_c) = Re_1 + jIm_1 \tag{26}$$

and the LPO signal may be substituted as follows.

[Expression 27]

$$\text{LPO signal:} \quad \frac{1}{2}(\sin(\theta + \delta\phi + \theta_x)) = \frac{1}{2}(\sin(\theta_c + \delta\phi)) \tag{27}$$
$$= \frac{1}{2}\exp(j(\theta_c + \delta\phi))$$
$$= Re_2 + jIm_2$$

In this case, a phase angle tan δφ of the input signal is expressed as follows.

[Expression 28]

$$\tan\delta\phi = \frac{Im_2 Re_1 - Re_2 Im_1}{Re_2 Re_1 + Im_2 Im_1} \tag{28}$$

After the phase angle tan δφ of the input signal is obtained using Expression (28), when tan−1δφ is computed, the phase difference signal δφ may be obtained.

A mass flow rate Q of the fluid to be measured is proportional to the phase angle and inversely proportional to a driving frequency F, and thus is expressed as follows.

[Expression 29]

$$Q = S(t) \cdot \delta\phi/F \tag{29}$$

where S(t) indicates a correction coefficient associated with a temperature of the measured fluid.

When the measured phase angle δφ and the driving frequency F are substituted into Expression (28), the mass flow rate Q may be calculated.

The mass flow rate Q obtained as described above is subjected to suitable scaling and unit conversion and may be output to an outside in various forms by adding subsequent processing such as analog output, pulse output, or serial communication.

<<Feature of Phase Measurement Method Using Frequency Conversion>>

According to a feature of the phase measurement system in the present invention, the signal may be sampled at the sampling interval unrelated to the frequency θ of the input signal which is obtained by converting, into the digital signal, by the A/D converter 31, the low-frequency left velocity signal (outlet-side velocity signal) which is detected by the left pick-off (left velocity sensor) 7 and extracted by the low-pass filter 30 and output therefrom, and which is input to the frequency conversion section 110. Therefore, the structure is very simple, no filter table is required, and very-high-speed computation may be achieved with a small computing error.

According to the phase measurement system of the present invention, even when a rapid change in frequency occurs in the input signal which is obtained by converting, into the digital signal, by the A/D converter 31, the low-frequency left velocity signal (outlet-side velocity signal) which is detected by the left pick-off (left velocity sensor) 7 and extracted by the low-pass filter 30, and which is input to the frequency conversion section 110, high-response following may be achieved by a frequency conversion feedback loop. The frequency after frequency conversion is directly measured to perform the phase measurement, and hence a frequency conversion error caused by the frequency conversion is minimized. Therefore, the system is suitable for very-high stable and accurate phase measurement.

In addition to the phase measurement, the frequency of the input signal may be simultaneously obtained based on the frequency after frequency conversion and the transmission frequency of the transmitter 120.

The obtained frequency is a frequency which is highly responsive and very stable because of the high-speed feedback loop.

Further, according to the phase measurement system in the present invention, there is little limitation on the phase measurement band by the input frequency of the input signal input to the frequency conversion section 110. Therefore, coupling with sensors having various driving frequencies may be realized and computing precision is not affected by the input frequency, and hence high-precision phase measurement may be always achieved.

Embodiment 3

The measurement tubes 2 and 3 including at least one flow tube or a pair of flow tubes, serving as measurement flow tubes, are operated by a driving device using the vibrator 6. The measurement tubes 2 and 3 including the one flow tube or the pair of flow tubes are alternately driven to vibrate the flow tubes. In a Coriolis flowmeter, a phase difference and/or a vibration frequency proportional to a Coriolis force acting on the measurement tubes 2 and 3 including the one flow tube or the pair of flow tubes are/is detected by a pair of velocity sensors or acceleration sensors corresponding to vibration detection sensors including the left pick-off (LPO) 7 and the right pick-off (RPO) 8, to thereby obtain a mass flow rate and/or density of a fluid to be measured.

The transmitter 120 for transmitting and outputting a modulatable frequency signal is provided in the Coriolis flowmeter.

A velocity sensor (for example, input signal (outlet-side velocity signal) input from left pick-off 7) from one of the pair of vibration detection sensors (left pick-off 7 and right pick-off 8) is converted into a digital signal by the first A/D converter 31. The first frequency conversion section 110 is provided to shift in frequency the input signal frequency θ to a specified constant frequency signal based on the output frequency θXn output from the transmitter 120, to thereby move the input signal frequency to a desired frequency band.

The second conversion section 140 is provided to shift in frequency, to a specified constant frequency signal, the input signal frequency θ obtained by converting, into a digital signal, by the second A/D converter 35, a velocity sensor (for example, input signal (inlet-side velocity signal) input from right pick-off 8) from the other of the pair of vibration detection sensors (left pick-off 7 and right pick-off 8), based on the output frequency θXn output from the transmitter 120, to thereby move the input signal frequency to a desired frequency band.

The frequency measurement section 160 is provided to measure the frequency of the first frequency signal which is obtained by converting as the constant frequency signal and output from the first frequency conversion section 110, and to output the measured frequency value of the first frequency signal to the transmitter 120, to thereby control the output frequency such that the frequency obtained by frequency conversion by the frequency conversion section 110 always becomes a constant frequency.

The phase difference measurement section 130 is provided to measure a phase difference between a first frequency signal obtained by conversion as a constant frequency signal by the first frequency conversion section 110 and a second frequency signal output as a converted constant frequency signal from the second frequency conversion section 140.

Further, the signal processing apparatus 100 is provided to obtain the phase difference between the first frequency signal output as the converted constant frequency signal from the first frequency conversion section 110 and the second frequency signal output as the converted constant frequency signal from the second frequency conversion section 140, to thereby serve as the Coriolis flowmeter.

DESCRIPTION OF SYMBOLS

1 Coriolis flowmeter
2, 3 measurement tube
4 detector converter
6 vibrator
7 left velocity sensor
8 right velocity sensor
9 temperature sensor
10 drive control section
11 phase measurement section
12 temperature measurement section
30, 34 low-pass filter
31, 35 A/D converter
70 vibration velocity sensor
80 vibration velocity signal computing device
85 frequency conversion section
90 transmitter
95 phase difference measurement unit
100 signal processing apparatus
110 frequency conversion section
111 multiplier
112 low-pass filter
120 transmitter
130 phase difference measurement unit
140 frequency conversion section
150 clock
160 frequency measurement section
161 multiplier
162 low-pass filter
163 transmitter for frequency measurement

The invention claimed is:

1. A signal processing method for a Coriolis flowmeter in which at least one flow tube or a pair of flow tubes which is included in a measurement flow tube is operated by a driving device using a vibrator to drive the at least one flow tube or the pair of flow tubes, and a phase difference or a vibration frequency proportional to a Coriolis force acting on the at least one flow tube or the pair of flow tubes is detected using a pair of vibration detection sensors when the at least one flow tube or the pair of flow tubes is vibrated, to thereby obtain a mass flow rate or a density of a fluid to be measured, the signal processing method comprising:
performing frequency conversion to add or subtract the frequency of a modulatable frequency signal to or from the frequency of a first digital signal obtained by converting a first input signal from one of the pair of vibration detection sensors into the first digital signal;
performing frequency conversion to add or subtract the frequency of the modulatable frequency signal to or from the frequency of a second digital signal obtained by converting a second input signal from the other one of the pair of vibration detection sensors into the second digital signal;
measuring a phase difference between (i) the frequency converted first digital signal and (ii) the frequency converted second digital signal;
obtaining a resonance frequency of the at least one flow tube or the pair of flow tubes based on the control signal, and calculating the density of the fluid to be measured based on the control signal.

2. The signal processing method according to claim 1, wherein the frequency conversion to subtract the frequency of the modulatable frequency signal from the frequency of the first digital signal is performed by (i) multiplying the modulatable frequency signal by the first digital signal and (ii) filtering a signal obtained as a result of the multiplication to extract only a low-frequency signal as the frequency converted first digital signal, and
wherein the frequency conversion to subtract the frequency of the modulatable frequency signal from the frequency of the second digital signal is performed by (i) multiplying the modulatable frequency signal by the second digital signal and (ii) filtering a signal obtained as a result of the multiplication to extract only a low-frequency signal as the frequency converted second digital signal.

3. The signal processing method according to claim 1, wherein the frequency conversion to add the frequency of the modulatable frequency signal to the frequency of the first digital signal is performed by (i) multiplying the modulatable frequency signal by the first digital signal and (ii) filtering a signal obtained as a result of the multiplication to extract only a high-frequency signal as the frequency converted first digital signal, and wherein the frequency conversion to add the frequency of the modulatable frequency signal to the frequency of the second digital signal is performed by (i) multiplying the modulatable frequency signal by the second digital signal and (ii) filtering a signal obtained as a result of the multiplication to extract only a high-frequency signal as the frequency converted second digital signal.

4. The signal processing method according to claim 1, wherein the frequency of the frequency converted first digital signal is ¼ of a sampling frequency used in A/D conversion performed on the first input signal to obtain the first digital signal, and wherein the frequency of the frequency converted second digital signal is ¼ of a sampling frequency used in A/D conversion performed on the second input signal to obtain the second digital signal.

5. A signal processing apparatus for a Coriolis flowmeter in which at least one flow tube or a pair of flow tubes which is included in a measurement flow tube is operated by a driving device using a vibrator to drive the at least one flow tube or to alternatively drive the pair of flow tubes, and a phase difference or a vibration frequency proportional to a Coriolis force acting on the at least one flow tube or the pair of flow tubes is detected using a pair of vibration detection sensors when the at least one flow tube or the pair of flow tubes is vibrated, to thereby obtain a mass flow rate or a density of a fluid to be measured, the signal processing apparatus comprising:

a transmitter for outputting a modulatable frequency signal;

a first frequency conversion section for (i) performing frequency conversion to add or subtract the frequency of the modulatable frequency signal to or from the frequency of a first digital signal obtained by converting, using a first A/D converter, a first input signal from one of the pair of vibration detection sensors into the first digital signal, (ii) performing frequency shifting on the frequency converted first digital signal so that the frequency of the frequency converted first digital signal is a desired frequency, and (iii) outputting the frequency shifted first digital signal;

a second frequency conversion section for (i) performing frequency conversion to add or subtract the frequency of the modulatable frequency signal to or from the frequency of a second digital signal obtained by converting, using a second A/D converter, a second input signal from the other one of the pair of vibration detection sensors into the second digital signal, (ii) performing frequency shifting on the frequency converted second digital signal so that the frequency of the frequency converted second signal is the desired frequency, and (iii) outputting the frequency shifted second digital signal; and a phase difference measurement section for measuring a phase difference between (i) the frequency shifted first digital signal output from the first frequency conversion section and (ii) the frequency shifted second digital signal output from the first frequency conversion section, wherein the phase difference measurement section obtains a resonance frequency of the at least one flow tube or the pair of flow tubes based on the measured phase difference, and calculates the density of the fluid to be measured based on the measured phase difference.

6. A signal processing apparatus for a Coriolis flowmeter in which at least one flow tube or a pair of flow tubes which is included in a measurement flow tube is operated by a driving device using a vibrator to drive the at least one flow tube or the pair of flow tubes, and a phase difference or a vibration frequency proportional to a Coriolis force acting on the at least one flow tube or the pair of flow tubes is detected using a pair of vibration detection sensors when the at least one flow tube or the pair of flow tubes is vibrated, to thereby obtain a mass flow rate or a density of a fluid to be measured, the signal processing apparatus comprising:

a transmitter for outputting a modulatable frequency signal;

a first frequency conversion section for performing frequency conversion to add or subtract the frequency of the modulatable frequency signal to or from the frequency of a first digital signal obtained by converting, using a first A/D converter, a first input signal from one of the pair of vibration detection sensors into the first digital signal, to adjust a frequency value obtained by the frequency conversion to a constant value; and a second frequency conversion section for performing frequency conversion to add or subtract the frequency of the modulatable frequency signal to or from the frequency of a second digital signal obtained by converting, using a second A/D converter, a second input signal from the other one of the pair of vibration detection sensors into the second digital signal, to adjust a frequency value obtained by the frequency conversion to a constant value.

7. A signal processing apparatus for a Coriolis flowmeter in which at least one flow tube or a pair of flow tubes which is included in a measurement flow tube is operated by a driving device using a vibrator to drive the at least one flow tube or to alternatively the pair of flow tubes, and a phase difference or a vibration frequency proportional to a Coriolis force acting on the at least one flow tube or the pair of flow tubes is detected using a pair of vibration detection sensors when the at least one flow tube or the pair of flow tubes is vibrated, to thereby obtain a mass flow rate or a density of a fluid to be measured, the signal processing apparatus comprising:

a transmitter for outputting a modulatable frequency signal a first frequency conversion section for (i) shifting the frequency of a first digital signal based on the frequency of the modulatable frequency signal output from the transmitter, the first digital signal being obtained by converting, using a first A/D converter, a first input signal from one of the pair of vibration detection sensors into the first digital signal and (ii) outputting the frequency shifted first digital signal;

a second frequency conversion section for (i) shifting the frequency of a second digital signal based on the frequency of the modulatable frequency signal output from the transmitter, the second digital signal being obtained by converting, using a second A/D converter, a second input signal from the other one of the pair of vibration detection sensors into the second digital signal and (ii) outputting the frequency shifted second digital signal; and a frequency measurement section for (i) measuring the frequency of the frequency shifted first digital signal output from the first frequency conversion section and (ii) outputting a value of the measured frequency to the transmitter, wherein the transmitter adjusts the modulatable frequency signal based on the value of the measured frequency received from the frequency measurement section so that the first frequency conversion section shifts the frequency of the first digital signal to a desired frequency and the second frequency conversion section shifts the frequency of the second digital signal to the desired frequency.

8. The signal processing apparatus according to claim 5, wherein the first frequency conversion section includes a first multiplier and a first low-pass filter, and the second frequency conversion section includes a second multiplier and a second low-pass filter, wherein the first frequency conversion section performs the frequency conversion to subtract the frequency of the modulatable frequency signal from the frequency of the first digital signal by (i) multiplying, using the first multiplier, the modulatable frequency signal output from the transmitter by the first digital signal and (ii) filtering, using the first low-pass filter, a signal obtained as a result of the multiplication to extract only a low-frequency signal as the frequency converted first digital signal, and wherein the second frequency conversion section performs the frequency conversion to subtract the frequency of the modulatable frequency signal from the frequency of the second digital signal by (i) multiplying, using the second multiplier, the modulatable frequency signal output from the transmitter by the second digital signal and (ii) filtering, using the second low-pass filter, a signal obtained as a result of the multiplication to extract only a low-frequency signal as the frequency converted second digital signal.

9. The signal processing apparatus according to claim 5, wherein the first frequency conversion section includes a first multiplier and a first high-pass filter, and the second frequency conversion section includes a second multiplier and a second high-pass filter, wherein the first frequency conversion section performs the frequency conversion to add the frequency of the modulatable frequency signal to the frequency of the first digital signal by (i) multiplying, using the first multiplier, the modulatable frequency signal output from the transmitter by the first digital signal and (ii) filtering, using the first high-pass filter, a signal obtained as a result of the multiplication to extract only a high-frequency signal as the frequency converted first digital signal, and wherein the second frequency conversion section performs the frequency conversion to add the frequency of the modulatable frequency signal to the frequency of the second digital signal by (i) multiplying, using the second multiplier, the modulatable frequency signal output from the transmitter by the second digital signal and (ii) filtering, using the second high-pass filter, a signal obtained as a result of the multiplication to extract only a high-frequency signal as the frequency converted second digital signal.

10. The signal processing apparatus according to claim 7, wherein the frequency measurement section includes:
a multiplier connected to the first frequency conversion section,
a low-pass filter connected to the multiplier, and
a transmitter for frequency measurement which is connected to the low-pass filter and receives an output signal from the low-pass filter,
wherein the multiplier (i) compares a phase of the frequency shifted first digital signal output from the first frequency conversion section with a phase of a signal output from the transmitter for frequency measurement and (ii) outputs a difference signal and a sum signal to the low-pass filter, wherein the low-pass filter filters the difference signal and the sum signal output from the multiplier to extract only the difference signal, and wherein the signal output from the transmitter for frequency measurement is controlled so that the difference signal extracted by the low-pass filter is approximately zero.

11. The signal processing apparatus according to claim 7, further comprising a clock for synchronizing an output of the first A/D converter and an output of the second A/D converter to synchronize (i) the first digital signal obtained by converting the first input signal from one of the pair of vibration detection sensors and (ii) the second digital signal obtained by converting the second input signal from one of the pair of vibration detection sensors.

12. The signal processing apparatus according to claim 7, wherein the phase measurement section measures the phase difference using a discrete Fourier transform or a fast Fourier transform.

13. A Coriolis flowmeter in which at least one flow tube or a pair of flow tubes which is included in a measurement flow tube is operated by a driving device using a vibrator to drive the at least one flow tube or to alternatively drive the pair of flow tubes, and a phase difference or a vibration frequency proportional to a Coriolis force acting on the at least one flow tube or the pair of flow tubes is detected using a pair of vibration detection sensors when the at least one flow tube or the pair of flow tubes is vibrated, to thereby obtain a mass flow rate or a density of a fluid to be measured, the Coriolis flowmeter comprising:

a transmitter for outputting a modulatable frequency signal;

a first frequency conversion section for (i) shifting the frequency of a first digital signal based on the frequency of the modulatable frequency signal output from the transmitter, the first digital signal being obtained by converting, using a first A/D converter, a first input signal from one of the pair of vibration detection sensors into the first digital signal and (ii) outputting the frequency shifted first digital signal;

a second frequency conversion section for (i) shifting the frequency of a second digital signal based on the frequency of the modulatable frequency signal output from the transmitter, the second digital signal being obtained by converting, using a second A/D converter, a second input signal from the other one of the pair of vibration detection sensors into the second digital signal and (ii) outputting the frequency shifted second digital signal; and a frequency measurement section for (i) measuring the frequency of the frequency shifted first digital signal output from the first frequency conversion section and (ii) outputting a value of the measured frequency to the transmitter, wherein the transmitter adjusts the modulatable frequency signal based on the value of the measured frequency received from the frequency measurement section so that the first frequency conversion section shifts the frequency of the first digital signal to a desired frequency and the second frequency conversion section shifts the frequency of the second digital signal to the desired frequency.

14. The signal processing apparatus according to claim 6, wherein the first frequency conversion section includes a first multiplier and a first low-pass filter, and the second frequency conversion section includes a second multiplier and a second low-pass filter, wherein the first frequency conversion section performs the frequency conversion to subtract the frequency of the modulatable frequency signal from the frequency of the first digital signal by (i) multiplying, using the first multiplier, the modulatable frequency signal output from the transmitter by the first digital signal and (ii) filtering, using the first low-pass filter, a signal obtained as a result of the multiplication to extract only a low-frequency signal as the frequency converted first digital signal, and wherein the second frequency conversion section performs the frequency conversion to subtract the frequency of the modulatable frequency signal from the frequency of the second digital signal by (i) multiplying, using the second multiplier, the modulatable frequency signal output from the transmitter by the second digital signal and (ii) filtering, using the second low-pass filter, a signal obtained as a result of the multiplication to extract only a low-frequency signal as the frequency converted second digital signal.

15. The signal processing apparatus according to claim 7,
wherein the first frequency conversion section includes a first multiplier and a first low-pass filter, and the second frequency conversion section includes a second multiplier and a second low-pass filter,
wherein the first frequency conversion section shifts the frequency of the first digital signal by (i) multiplying, using the first multiplier, the modulatable frequency signal output from the transmitter by the first digital signal and (ii) filtering, using the first low-pass filter, a signal obtained as a result of the multiplication to extract only a low-frequency signal as the frequency shifted first digital signal, and
wherein the second frequency conversion section shifts the frequency of the second digital signal by (i) multiplying, using the second multiplier, the modulatable frequency signal output from the transmitter by the second digital signal and (ii) filtering, using the second low-pass filter, a signal obtained as a result of the multiplication to extract only a low-frequency signal as the frequency shifted second digital signal.

16. The signal processing apparatus according to claim 6,
wherein the first frequency conversion section includes a first multiplier and a first high-pass filter, and the second frequency conversion section includes a second multiplier and a second high-pass filter,
wherein the first frequency conversion section performs the frequency conversion to add the frequency of the modulatable frequency signal to the frequency of the first digital signal by (i) multiplying, using the first multiplier, the modulatable frequency signal output from the transmitter by the first digital signal and (ii) filtering, using the first high-pass filter, a signal obtained as a result of the multiplication to extract only a high-frequency signal as the frequency converted first digital signal, and wherein the second frequency conversion section performs the frequency conversion to add the frequency of the modulatable frequency signal to the frequency of the second digital signal by (i) multiplying, using the second multiplier, the modulatable frequency signal output from the transmitter by the second digital signal and (ii) filtering, using the second high-pass filter, a signal obtained as a result of the multiplication to extract only a high-frequency signal as the frequency converted second digital signal.

17. The signal processing apparatus according to claim 7,
wherein the first frequency conversion section includes a first multiplier and a first high-pass filter, and the second frequency conversion section includes a second multiplier and a second high-pass filter,
wherein the first frequency conversion section shifts the frequency of the first digital signal by (i) multiplying, using the first multiplier, the modulatable frequency signal output from the transmitter by the first digital signal and (ii) filtering, using the first high-pass filter, a signal obtained as a result of the multiplication to extract only a high-frequency signal as the frequency shifted first digital signal, and
wherein the second frequency conversion section shifts the frequency of the second digital signal by (i) multiplying, using the second multiplier, the modulatable frequency signal output from the transmitter by the second digital signal and (ii) filtering, using the second high-pass filter, a signal obtained as a result of the multiplication to extract only a high-frequency signal as the frequency shifted second digital signal.

* * * * *